US009335413B2

(12) United States Patent
Weber-Grabau

(10) Patent No.: US 9,335,413 B2
(45) Date of Patent: May 10, 2016

(54) OBJECT DETECTION SYSTEMS

(71) Applicant: onVector Technology, LLC, Sunnyvale, CA (US)

(72) Inventor: Michael Weber-Grabau, Sunnyvale, CA (US)

(73) Assignee: onVector Technology LLC, Sunnyvale, CA (US)

( * ) Notice: Subject to any disclaimer, the term of this patent is extended or adjusted under 35 U.S.C. 154(b) by 0 days.

(21) Appl. No.: 14/624,540

(22) Filed: Feb. 17, 2015

(65) Prior Publication Data
US 2015/0234049 A1     Aug. 20, 2015

Related U.S. Application Data

(60) Provisional application No. 61/940,974, filed on Feb. 18, 2014, provisional application No. 61/968,296, filed on Mar. 20, 2014.

(51) Int. Cl.
G01N 21/00   (2006.01)
G01S 17/02   (2006.01)
G01N 21/68   (2006.01)
G01N 21/64   (2006.01)
G01J 3/02    (2006.01)
H01J 37/32   (2006.01)
G01V 8/20    (2006.01)

(52) U.S. Cl.
CPC ............... *G01S 17/026* (2013.01); *G01J 3/02* (2013.01); *G01N 21/00* (2013.01); *G01N 21/64* (2013.01); *G01N 21/68* (2013.01); *G01V 8/20* (2013.01); *H01J 37/32935* (2013.01)

(58) Field of Classification Search
CPC ... H01J 37/32935; G01N 21/64; G01N 21/68; G01N 2015/1037; G01J 3/02
USPC ...................................................... 356/72–73
See application file for complete search history.

(56) References Cited

U.S. PATENT DOCUMENTS

| 4,906,835 A | 3/1990 | Betts |
| 5,539,198 A | 7/1996 | McMichael et al. |
| 6,766,251 B2 | 7/2004 | Mafra-Neto et al. |
| 7,001,038 B2 * | 2/2006 | Bock et al. ................... 362/125 |
| 7,071,829 B2 | 7/2006 | Gardner, Jr. et al. |
| 7,511,624 B2 | 3/2009 | Shaw et al. |
| 8,705,017 B2 | 4/2014 | Hyde et al. |

(Continued)

FOREIGN PATENT DOCUMENTS

WO   WO2012112785   8/2012

OTHER PUBLICATIONS

International Search Report and Written Opinion of the International Search Authority mailed May 14, 2015 in Patent Cooperation Treaty Application No. PCT/US2015/016228, filed Feb. 17, 2015.

(Continued)

*Primary Examiner* — Abdullahi Nur
(74) *Attorney, Agent, or Firm* — Carr & Ferrell LLP

(57) ABSTRACT

Object detection systems are provided herein. An example system includes an enclosure formed by a sidewall to define an interaction volume, at least one light source for illuminating the interaction volume with a light, at least one light sensor that senses disturbances in light intensity due to scattering, reflection, or absorption of the light by objects within the interaction volume, and a controller that is configured to detect an object or object behavior within interaction volume based on the disturbances in the light intensity.

26 Claims, 15 Drawing Sheets

(56) References Cited

U.S. PATENT DOCUMENTS

| | | |
|---|---|---|
| 2002/0185605 A1 | 12/2002 | Shuman et al. |
| 2003/0218543 A1 | 11/2003 | Gardner, Jr. et al. |
| 2005/0236481 A1 | 10/2005 | Gascoyne et al. |
| 2006/0254522 A1 | 11/2006 | Shaw et al. |
| 2009/0097019 A1 | 4/2009 | Baker |
| 2010/0063744 A1 | 3/2010 | Golombek et al. |
| 2010/0186284 A1 | 7/2010 | Hyde et al. |
| 2011/0090485 A1 | 4/2011 | Cronin et al. |
| 2013/0204581 A1 | 8/2013 | Park et al. |

OTHER PUBLICATIONS

Richards. "Photoelectric Cell Observations of Insects in Flight", Nature (1955), vol. 175, pp. 128-129.

Znenyu Li et al. "Automated Identification of Mosquito (Diptera: Culicidae)Wingbeat Waveform by Artificial Neural Network", Artificial Intelligence Applications and Innovations (2005) pp. 483-489, Springer.

Batista et al. "SIGKDD Demo: Sensors and Software to Allow Computational Entomology, an Emerging Application of Data Mining", Proceedings of the 17th ACM SIGKDD (2011), pp. 761-764, ACM Digital Library.

Batista et al. "Counting and Classifying Mosquitoes from a Distance with Ultra Cheap Sensors", American Mosquito Control Association 77th conference (2011).

Eomann Keogh et al. "Using the UCR WBF Sensor", http://web.archive.org/web/20120617051813/http://www.cs.ucr.edu/~eamonn/CE/Sensors.pdf (2013).

* cited by examiner

OBJECT DETECTION SYSTEMS

CROSS REFERENCE TO RELATED APPLICATIONS

This application claims the priority benefit of U.S. Provisional Application Ser. No. 61/940,974, filed on Feb. 18, 2014, and U.S. Provisional Application Ser. No. 61/968,296, filed on Mar. 20, 2014, all of which are hereby incorporated by reference herein in their entireties including all references cited therein.

FIELD OF THE INVENTION

The present technology pertains to object detection systems, and more particularly, but not by limitation, to systems that are configured to detect the presence of objects in an illuminated interaction volume to determine object counts, object size, object movement, and so forth.

SUMMARY

According to some embodiments, the present technology is directed to an object detection system, comprising: (a) an enclosure formed by a sidewall to define an interaction volume; (b) at least one light source for illuminating the interaction volume with a light; (c) at least one light sensor that senses disturbances in light intensity due to scattering, reflection, or absorption of the light by objects within the interaction volume; and (d) a controller that is configured to detect an object or object behavior within interaction volume based on the disturbances in the light intensity.

Some embodiments include the controller being further configured to: (1) modulate a frequency of the at least one light source to account for ambient light in the interaction volume; and (2) detect interactions by the insect within the interaction volume by: (i) detecting modifications of the modulated light by the objects; and (ii) differentiating the ambient light from the modulated light through signal processing.

In one embodiment, a modulation frequency is chosen to be above a frequency of fluctuations or oscillations of the ambient light.

In another embodiment, differentiating the ambient light from the modulated light through signal processing comprises suppressing a constant or variable background signal caused by an ambient light source, wherein the background signal comprises frequencies in the range of approximately 0 Hz to approximately 120 Hz, inclusive.

In yet another embodiment, the at least one light sensor comprises at least one of: (A) a bright field sensor disposed in a location inside or near the sidewall of the illuminated volume so as to allow the light to contact the bright field sensor, the bright field sensor indicating a reduction in the light intensity of the light; and (B) a dark field sensor disposed in a location inside or near the sidewall of the illuminated volume so as to prevent the light from contacting the dark field sensor, the dark field sensor indicating an increase in the light intensity of the light.

In one embodiment, the controller is further configured to detect a size of the objects.

In some embodiments, the at least one light source comprises a plurality of light sources. The controller is further configured to modulate a frequency of light emitted by each of the plurality of light sources such that the frequency of each of the plurality of light sources is different from one another.

According to some embodiments, the system further comprises an attracting light source.

In yet another embodiment, the at least one light sensor is positioned in a location comprising any of: (1) a location suitable for sensing light that passes through and exits the interaction volume; (2) a location suitable for sensing light scattered or reflected but not light passing through and exiting the interaction volume; and (3) a location for sensing the light intensity present in the interaction volume.

In some embodiments, the at least one sensor has a spectral sensitivity response with a maximum near a peak emission of a light source.

In one embodiment, the at least one light sensor comprises a plurality of light sensors, wherein each of a plurality of light sensors has a maximum sensitivity near a peak emission of at least one of a plurality of light sources.

In another embodiment, the controller is further configured to time stamp signals received from the at least one light sensor.

In some embodiments, the objects sensed are insects, further wherein the controller is further configured to detect and record a sequence, the sequence comprising a first time at which an insect is not present in the interaction volume, a second time at which an insect is present in the interaction volume, and a third time at which the insect is not present in the interaction volume, wherein detecting the sequence indicates a count of an insect in the interaction volume.

In one embodiment, the objects sensed are insects, further wherein the controller is further configured to calculate a wing beat frequency of an insect by detecting a waveform of light that is resultant from a modulation of light intensity by the wing beat frequency.

In one embodiment, the objects sensed are insects, further wherein the controller is further configured to calculate a wing beat frequency of an insect by: (1) modulating the light intensity of the at least one light source with a carrier frequency that is higher than the wing beat frequency of the insect to create a modulated waveform; and (2) detecting a waveform of light that is resultant from a modulation of the carrier frequency by the wing beat frequency.

In an embodiment, the controller comprises an envelope filter that removes the carrier frequency from the modulated waveform.

In some embodiments, an inner surface of the enclosure is a retro-reflective surface reflecting the light emitted by the light source.

In yet other embodiments, the interaction volume comprises a funnel and a trap disposed on opposing ends of the interaction volume.

In one embodiment, the at least one light source comprises any of a light emitting diode, a line laser, or combinations thereof.

According to some embodiments, the at least one sensor comprises any of a photodiode, a phototransistor, a charge coupled device, a position-sensitive detector, a solar cell, a photovoltaic cell, an antenna, a thermopile, or any combinations thereof.

In one embodiment, at least one light sensor comprises an array comprising a plurality of individual photodiodes, the plurality of individual photodiodes being electrically coupled in series, at least one of the plurality of individual photodiodes is masked by an object so as to receive less light than non-masked ones of the plurality of individual photodiodes in order to reduce a current through the array, which results in an increase in a sensitivity of the non-masked ones of the plurality of individual photodiodes.

In one embodiment, at least one light sensor comprises an array comprising a plurality of individual photodiodes, the plurality of individual photodiodes being electrically coupled in parallel, at least one of the plurality of individual photodiodes is masked so as to receive less light than non-masked ones of the plurality of individual photodiodes in order to reduce a current through the array.

According to some embodiments, the present technology is directed to an object detection system comprising: (a) a light source comprising a linear array of light emitting devices; (b) a light sensor comprising at least one linear array of photodiodes and at least one linear array of solar cells, wherein at least one of the solar cells is masked so as to receive less light than non-masked ones of the solar cells in order to reduce a current through the array, which results in an increase in a sensitivity of the non-masked ones of the solar cells; (c) an interaction volume defined by a space between the light source and the light sensor, wherein the space between the light source and the light sensor allows for uniform light intensity throughout the interaction volume; and (d) wherein the light sensor senses disturbances in the light intensity indicative of a presence of an object in the interaction volume.

BRIEF DESCRIPTION OF THE DRAWINGS

The accompanying drawings, where like reference numerals refer to identical or functionally similar elements throughout the separate views, together with the detailed description below, are incorporated in and form part of the specification, and serve to further illustrate embodiments of concepts that include the claimed disclosure, and explain various principles and advantages of those embodiments.

The methods and systems disclosed herein have been represented where appropriate by conventional symbols in the drawings, showing only those specific details that are pertinent to understanding the embodiments of the present disclosure so as not to obscure the disclosure with details that will be readily apparent to those of ordinary skill in the art having the benefit of the description herein.

DETAILED DESCRIPTION

Figure 1:
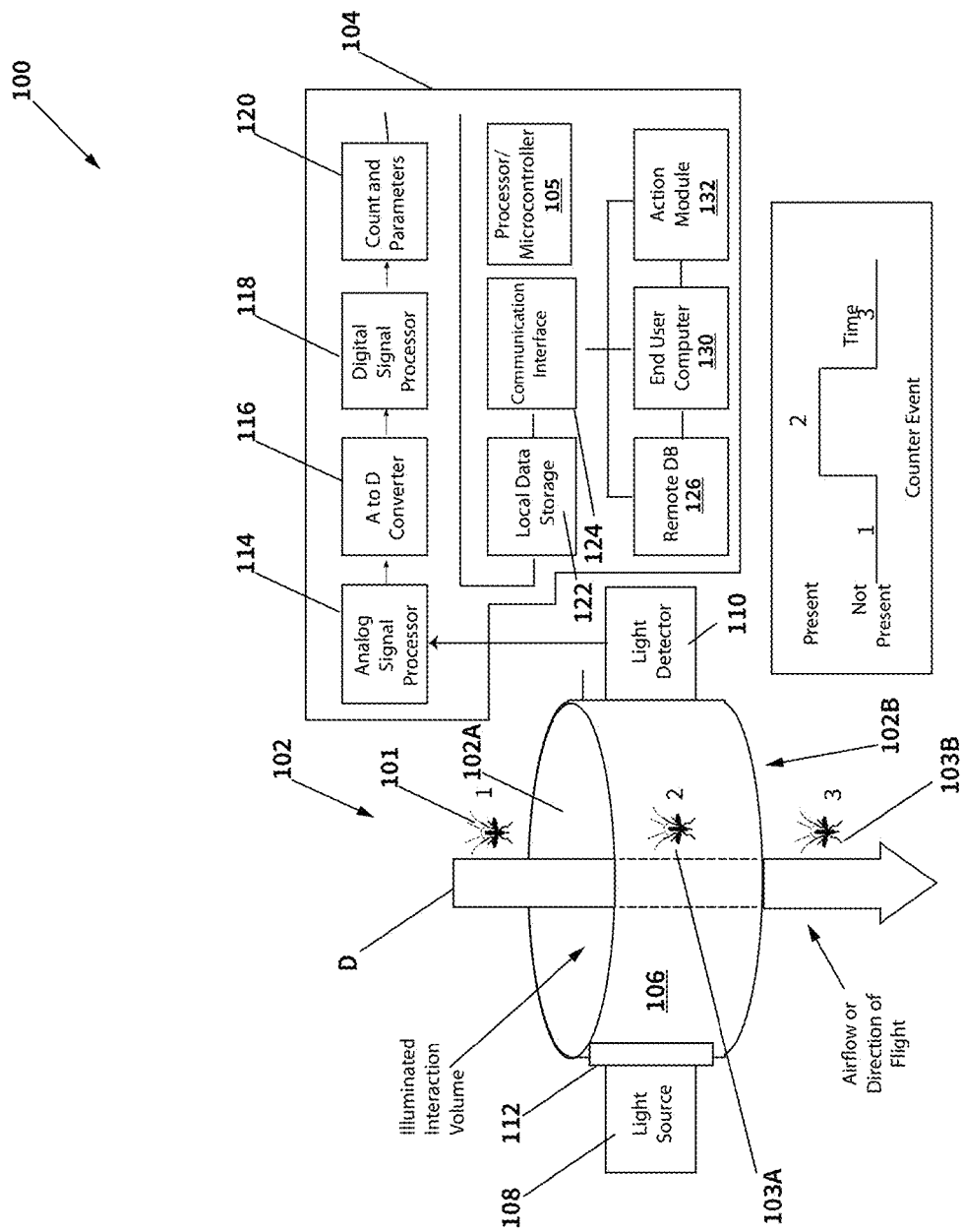
FIG. 1 is a schematic diagram of an example object detection system of the present technology.

The present disclosure is now described more fully with reference to the accompanying drawings, in which example embodiments of the present disclosure are shown. The present disclosure may, however, be embodied in many different forms and should not be construed as necessarily being limited to the example embodiments set forth herein. Rather, these example embodiments are provided so that the disclosure is thorough and complete, and fully conveys the concepts of the present disclosure to those skilled in the art. Also, features described with respect to certain example embodiments may be combined in and/or with various other example embodiments. Different aspects and/or elements of example embodiments, as disclosed herein, may be combined in a similar manner. Further, at least some example embodiments may individually and/or collectively be components of a larger system, wherein other procedures may take precedence over and/or otherwise modify their application. Additionally, a number of steps may be required before, after, and/or concurrently with example embodiments, as disclosed herein. Note that any and/or all methods and/or processes, at least as disclosed herein, can be at least partially performed via at least one entity, at least as described herein, in any manner, irrespective of the at least one entity have any relationship to the subject matter of the present disclosure.

In agriculture and public health, surveillance of insects with respect to species and abundance is important. There are many insects that are pests (damaging property and crops), nuisances (causing discomfort to people and animals), disease-causing vectors, or a combination. Vectors transmit microorganisms that cause disease or otherwise harm people, animals, crops and beneficial plants. Only female insects needing blood meals to reproduce bite humans and transmit disease. Of particular concern are malaria, Dengue fever, West Nile Virus, elephantiasis and many other serious and often fatal diseases.

Currently, insect surveillance is done by entomologists manually counting insects caught in traps. This approach is time-consuming, labor-intensive and costly. Moreover, it does not provide real-time data, i.e. there are delays until appropriate action can be taken. Also, the data density is usually sparse.

A good example is given by the recent appearance in the US of an important disease vector, the mosquito species *aedes aegypti*. This mosquito is not indigenous to the US and is of great concern because of its ability to transmit dengue fever and its adaption to human habitation. Mosquito control agencies desire to eradicate the mosquito before it has a chance to get established and spread from the initial area of introduction. The process is to set up traps around a location where the invading mosquito species was found, attempt to determine how far it has spread, and apply chemicals to kill adults and larvae in targeted areas. Other control measures include reducing breeding grounds such as standing water in containers around houses. The efficacy of treatment is confirmed by trapping. Unfortunately, only a few (often less than 10) traps are typically used in areas that may cover many square miles. This is due to the labor required for setting traps, retrieving the catch and taking it to a laboratory for counting and classification. Furthermore, surveillance of the population over extended periods of time to optimize control measures and verify their efficacy is often not possible due to budget constraints.

While most mosquito control measures involve applying chemicals that kill adults or larvae, alternative biological methods are currently under development. These methods involve the breeding and release of male mosquitoes that have been modified to render eggs unviable or to produce sterile offspring. The concept is that the released male mosquitoes compete with wild males and mate with at least a portion of the wild female population thus reducing offspring capable of transmitting disease. Repeated releases gradually reduce the wild population until it gets so small that either effective disease transmission is no longer possible, or the mosquito population collapses or remains at a very low level. These methods depend on the release of modified males only; females are not desired and detrimental to the effort. One strategy is to sort young adult mosquitoes, and eliminate females, before release. This process is currently based on size or weight differences between male and female mosquito larvae and much less than 100% accurate. A detector capable of differentiating males and females in combination with a sorting device to separate females or a killing device to kill them would solve this problem. Mosquito sex can be determined by measuring wing beat frequency. Typical mosquito wing beat frequencies are around 1 kHz, differing by species, sex, age and other factors. However, given just one species and controlled conditions, the difference in wing beat frequency (lower in females) can be used to positively identify females and eliminate them from the population of biologically modified mosquitoes to be released.

While effective traps exist to attract and catch insects, no devices to count, classify or sort insects automatically are currently available in the marketplace. It is therefore desirable to provide an object detection system (ODS) which can be used to count insects, and to provide information about wing beat frequency, size and anatomical features of the insect as well as other biological or environmental parameters. Moreover, it is desirable to provide an object detection system that has communication means to remotely report at least the number of detected objects such as insects, and is in communication with trapping, sorting or killing means for at least a portion of the detected insects.

In some embodiments, the present technology provides a volume of space is irradiated with light from a light source. Objects in the volume of light (for example, flying insects) modify the light intensity by absorbing, scattering and reflecting light, resulting in a change of light intensity in the volume ("bright field") and outside the volume ("dark field"). A light-sensitive detector comprising multiple light-sensitive elements is placed in a location suitable for detecting light from the volume. The light-sensitive detector is connected to a means for signal processing for object presence determination. When objects enter the volume of space from one direction and thereafter leave it in the same or another direction, the detector records a sequence of transitions of the object presence signal that is used for counting the objects. If the objects are insects, the detected light also carries information about biological parameters that is extracted by signal processing and allows classification. The detection system is in communication with a database and a cell phone or computer user or other means capable of taking an action.

The term "light" is used to refer to the electromagnetic radiation used in the invention. Commonly, "light" designates electromagnetic radiation in the ultraviolet (UV), visible, infrared (IR) and microwave part of the electromagnetic spectrum. Light in all these spectral ranges may be used in the present technology.

These and other advantages of the present technology are described with reference to the collective drawings.

Referring now to FIG. 1, an example object detection system 100 (also referred to as device 100) is illustrated. The system generally comprises an interaction volume 102 and a controller 104.

In some embodiments, the system 100 according to the present technology comprises at least one light source, an interaction volume, at least one light sensor, and means for analog-to-digital conversion, signal processing, counting, and data communication. Another attribute of the system is that has the ability to attach time and date stamps to all recorded data, and is in communication with a remote database or human operators. In some embodiments, the system 100 comprises means to take an action such as trapping, killing, identifying or sorting, if the objects are insects.

According to some embodiments, the interaction volume 102 includes open ends 102A and 102B that allow for the passage of objects, such as mosquitos 101, 103A, and 103B through the interaction volume 102. In some embodiments, air passes through the interaction volume 102 in a direction D.

In some embodiments, the interaction volume 102 is an enclosure formed from a sidewall 106. The sidewall 106 can be continuous or comprised of sidewall segments in some embodiments. The sidewall 106 illustrated forms a cylindrical enclosure although other shapes are also likewise contemplated for use in accordance with the present technology. The enclosure defines a three dimensional volume. Again, the volume illustrated FIG. 1 is cylindrical, but other three dimensional shapes such as a cone, a cube, a pie wedge, a box, a cuboid, or even an irregularly shaped three dimensional volume.

In one embodiment, the interaction volume 102 contains a plurality of smaller volumes that are overlapping, adjacent or separated by small volumes of space.

In some embodiments, the interaction volume 102 has a cross section and a height, with height being the smallest of three dimensions. The cross section is at least one centimeter squared and the height is at least one tenth of a millimeter.

In some embodiments, the sidewall 106 is manufactured from a transparent or semi-transparent material. In another embodiment, the sidewall 106 is manufactured from an opaque material. In yet other embodiments, the sidewall 106 is manufactured from sections of transparent material and opaque material. The exact configuration of the sidewall 106 depends upon the light sources and light sensors used for the device 100, as will be described in greater detail below.

In some embodiments, the device 100 includes a light source 108 and a light detector or sensor 110. Both the light source 108 and light detector 110 are positioned in association with the device 100. The exact position of both the light source 108 and light sensor 110 depend upon the composition of both the light source 108 and light sensor 110.

In some embodiments, the light source 108 is a light emitting diode (LED) or an array of LEDs that emit light through the sidewall 106. The LED(s) light will emit light at a particular frequency or range of frequencies. Thus, the light sensor 110 is disposed on an opposing side of the sidewall 106 and is configured to measure light relative to that frequency or frequencies.

In another embodiment, the light source 108 comprises an illuminated strip of LEDs, or a backlight similar to light sources used in flat panel displays or car instrument panels.

In one embodiment, the light source 108 is a light emitting laser. For example, the light source 108 could comprise a line laser.

In one embodiment, the light source 108 emits light in the UV or visible range. In one embodiment, the light source 108 emits light in the infrared (IR) range. IR light is present in an ambient light background at a level lower than visible or UV light and thus IR illumination facilitates background suppression. Also, certain insects such as mosquitoes do not perceive IR light, so an IR light emitting source can be used in embodiments where the system 100 is configured to detect mosquitoes.

The light emitted by the light source 108 can be shaped by means such as lenses, reflectors, line generators and diffusers. For example, the device 100 can include a light shaping member 112 that can include any combination (or one of) lenses, reflectors, line generators and diffusers—just to name a few.

In one embodiment, the light emitted from a light source is distributed throughout the interaction volume 102 using at least one light shaping member 112 selected from a list comprising lenses, Fresnel lenses, cylindrical lenses, mirrors, reflectors, retro-reflectors, filters (comprising high-pass, low-pass, band-path and dichroic), beam blocks, beam splitters, apertures, beam dumps, shutters, absorbers, diffusers and laser line generators.

Objects in the interaction volume 102 interact with the light produced by the light source 108. Example modes of interaction comprise absorption, reflection and scattering. The light interaction/modification results in change in an intensity of light from the light source 108, such as a reduction in light intensity. Again, at least one light sensor 110 is placed in a location suitable for detecting the change in light level within the interaction volume 102.

In one embodiment, the light source 108 emits a collimated beam (for example, a laser spot) or a thin sheet of light (for example, a laser line). In another embodiment, the light source 108 resembles a floodlight emitting light into a range of angles (for example, an LED).

The light sensor 110 can include one or a plurality of light sensors. In some embodiments, the light sensor 110 comprises at least one light-sensitive element that is placed in at least one location relative to the enclosure. In one embodiment, the location where the light sensor is located is suitable for sensing light that passes through and exits the enclosure. In another embodiment, the location where the light sensor is a location suitable for sensing light scattered or reflected, but not on a straight line between the light source 108 and the light sensor 110 disposed near an exit of the enclosure. In yet another embodiment, the location where the light sensor 110 is located is selected for suitable sensing of the light intensity present within in the enclosure.

In some embodiments, the light sensor 110 comprises a light-sensitive element chosen from the list comprising photodiodes, phototransistors, charge coupled devices, position-sensitive detectors, solar cells/panels, antennas, and thermopiles. In one embodiment, a light sensor 110 comprises a single light-sensitive element (for example a photodiode or phototransistor). In one embodiment, a light sensor 110 comprises a linear array of light-sensitive elements (for example: a photodiode array). In one embodiment, a light sensor 110 comprises an imaging device such as a two-dimensional matrix of light-sensitive elements. Image sensors may be of the type used in consumer electronics (e.g., cell phones cameras) and based on photodiodes, charge controlled devices, or complementary metal oxide semiconductor pixels. Another light sensor 110 is a high-speed camera. In one embodiment, a light sensor 110 comprises a spectrometer. In one embodiment, a light sensor 110 comprises a line scan camera. To be sure, combinations of these various light sensors can also likewise be utilized. Again, the exact type of light sensor(s) selected will depend upon the light source(s) utilized and the type of objects being sensed.

To be sure, there are many locations that can be chosen to position a light source and a light sensor relative to the interaction volume 102, in part depending on the configuration of the object-detecting device such as the shape of the interaction volume 102, and the combination with a device to sort the objects according to a property of the object.

In one embodiment, the spectral sensitivity response of a light sensor has a maximum near the peak emission of a light-emitting element. In one embodiment, each of a plurality of light-sensitive elements has maximum sensitivity near the peak emission of at least one of a plurality of light-emitting elements. In one embodiment, a light sensor is equipped with a filter to transmit the wavelength of a light-emitting element. In one embodiment, a plurality of light sensing elements senses light from light-emitting elements with different modulation frequencies.

When the light sensor 110 is continuously illuminated by a light source 108, an object entering the interaction volume 102 will modify the light intensity. A modification of the light intensity includes, in some instances, a reduction of light intensity at the light sensor 110. This change in intensity is resulting from the light sensor 110 operating in bright field mode.

Since an object can enter the interaction volume 102 at any location, either focusing or reflecting optics are needed if the light sensor 110 has a small area. An example photodiode has an active area of about seven square millimeters. The present technology, in some embodiments, employs a large-area detector to eliminate the need for such optics.

The light source 108 and light sensor 110 are both controlled by the controller 104. In some embodiments, the controller 104 comprises a processor 105, an analog signal processor 114, an analog to digital converter (also referenced as A/D converter) 116, a digital signal processor 118, a count and other parameters module 120, a local data storage 122, a data communication interface (also referenced as a communication module) 124, a remote database 126, an end user computer 130, and an action module 132.

As used herein, the terms "module" and/or "engine" may also refer to any of an application-specific integrated circuit ("ASIC"), an electronic circuit, a processor (shared, dedicated, or group) that executes one or more software or firmware programs, a combinational logic circuit, and/or other suitable components that provide the described functionality.

In some embodiments, the controller 104 controls the light source 108 to emit light into the interaction volume 102. In one embodiment, the intensity of light source 108 is modulated by the controller 104 with a periodic waveform or carrier frequency using the digital signal processor 118. The frequency utilized can be selected from a list comprising the following types: a rectangular wave and a sine wave.

In one embodiment, the modulation frequency is greater or equal to 100 Hz. In another embodiment, the modulation frequency is 3 kHz, 5 kHz, 10 kHz, 30 kHz, 33 kHz, 36 kHz, 38 kHz, 40 kHz and 56 kHz. It is not necessary for a modulated light source to have a minimum intensity of zero or to even be periodic; rather, the property that the intensity is time-dependent following a predefined pattern is the advantageous to the operation of the device 100.

In one embodiment, the controller 104 controls the digital signal processor to control a plurality of light-emitting elements such that each is modulated at different frequencies.

It should be noted that the change in light due to the presence of an object in the interaction volume 102 is not constant, rather it is a time-dependent function of the object's speed, shape, orientation, size, motion such as wing beat (which changes the amount of light in a rhythmic pattern), and other intrinsic and environmental parameters.

The light sensor 110 also is subject to impingement by ambient background light, such as light not originating from the light source 108 or object but from sources nearby the device 100. The ambient background light can be significant and possibly exceed the signal generated by an object within the interaction volume 102.

A relatively slowly changing ambient light background, as well as a constant light level from the illumination can effectively be separated from the object signal by filtering of a detector output. For example, the analog signal processor 114 can comprise high-pass filter or a band-pass filter to suppress a constant offset or specific frequencies such as a 100 or 120 Hz frequency entering the interaction volume 102 from an artificial light source, respectively. Alternatively, the light intensity of the light source 108 can be modulated by the controller 104 using a carrier frequency. A digital signal processor 118 can be used to extract an object signal by separating the carrier frequency from the signal received by the light sensor 110. That is, the signal received by the light sensor 110 is a combination of the object signal and ambient light signal. When the carrier frequency is removed, only the object signal remains.

When more than one light source is used, the controller 104 may impose upon each one of the light sources a different modulation frequency or light wavelength. This allows the interaction volume 102 to have different regions and provide an indication of the object's location with greater precision that when only one light source is utilized.

According to the present technology, objects such as insects enter the interaction volume 102 at a point in space, remain there for a period of time, and leave it at another point in space. Usually, the objects move in only one direction. For example, insects are either flying towards an attractant or being swept along by airflow through the interaction volume 102.

When objects enter the interaction volume 102, the light sensor 110 picks up a change in light intensity characteristic of their presence, and another change in light intensity when the objects leave the volume. While the objects remain in the interaction volume 102, light level changes encode additional information about the object such as biological and environmental information. Using analog and digital signal processing and counting means, these light level changes are processed by the controller 104 and result in data indicating object count as well as certain other information.

For example, a bigger object leads to a larger change in light level as sensed by the light sensor 110. Insects beating their wings while in the interaction volume 102 cause changing amounts of absorbed, scattered and reflected light corresponding to the wing beat frequency. Multiple objects simultaneously present in the interaction volume 102 result in a signal that is a combination of individual object signals.

The controller 104 is configured to provide a variety of signal processing features. The light source 108, ambient light, noise and the object-dependent signal are sensed by the light sensor 110 and contribute to a light sensor output.

The output of the light sensor 110 depends on the number of objects present in the interaction volume 102. While ambient light is constant or slowly varying, the light absorbed, reflected, scattered or otherwise modified by the objects in the interaction volume 102 varies over time. According to the present technology, the object-dependent signal is extracted from the light sensor 110 output with a combination of analog and digital signal processing, as mentioned above.

Initially, a time-dependent signal is generated. The digital signal processor 118 uses local data storage 122 to record time-dependent signals and a computing means such as a microprocessor or microcontroller (referred to as processor 105). A microcontroller comprises a microprocessor and input/output functions including analog-to-digital converter 116.

Some embodiments of the present technology comprise a method for data acquisition and signal processing. For example, the controller 104 can be configured to provide analog signal conditioning for the output of the light sensor 110.

In some embodiments, the controller 104 is configured to perform analog to digital signal conversion of the output of the light sensor 110 using the analog to digital converter 116 and digital signal processor 118. The controller 104 can also use analog signal conditioning, demodulation and amplification using an integrated circuit resulting in a bi-level (high/low) electronic "object presence" signal. The controller 104 also employs A/D conversion and digital signal processing.

Examples for analog signal conditioning are high-pass, low-pass and band-pass filters.

In one embodiment, the A/D converter 116 uses a binary input port on a microcontroller. In one embodiment, the A/D converter 116 is an analog input port on a microcontroller. In one embodiment, the A/D converter 116 uses is an integrated circuit connected to a digital input (such as a serial port) on a microcontroller.

Analog as well as digital signal processing comprise one or more techniques from the list comprising filters, amplification, comparison, thresholding, correlation, deconvolution, pattern recognition and demodulation —just to name a few.

In operation, when an object enters the interaction volume 102 and thereafter leaves, the controller records a sequence of transitions (no object present->object present->no object present), which is used for counting objects. The light produced by the light source 108 also carries information about objects such as wing beat frequency, size and other features of the object that is extracted from a light sensor output using the signal processing means of the controller 104.

The communication module 124 can comprise an interface for bi-directional data communication to transfer insect counts and other information between the device 100, a remote database 126, an end user computer 130, and an action module 132. Information from the database is used for monitoring, report generation and initiation of action. Bi-directional communication also allows a user to configure the device 100, for example, reset the object counter to zero, initiate object counting, or enter the GPS location of the device 100 deployed in the field.

In one embodiment, the communication module 124 comprises at least one of a wired connection; a wireless connection; a TCP/IP connection; a removable memory device (e.g. flash card or USB stick); a cellular modem; a WiFi adapter; and a Bluetooth adapter; active and passive RFID—just to name a few.

In one embodiment, the device 100 is configured to attach time and date stamps to all data being recorded such as insect present events, biological parameters and environmental sensor readings.

Figure 2:
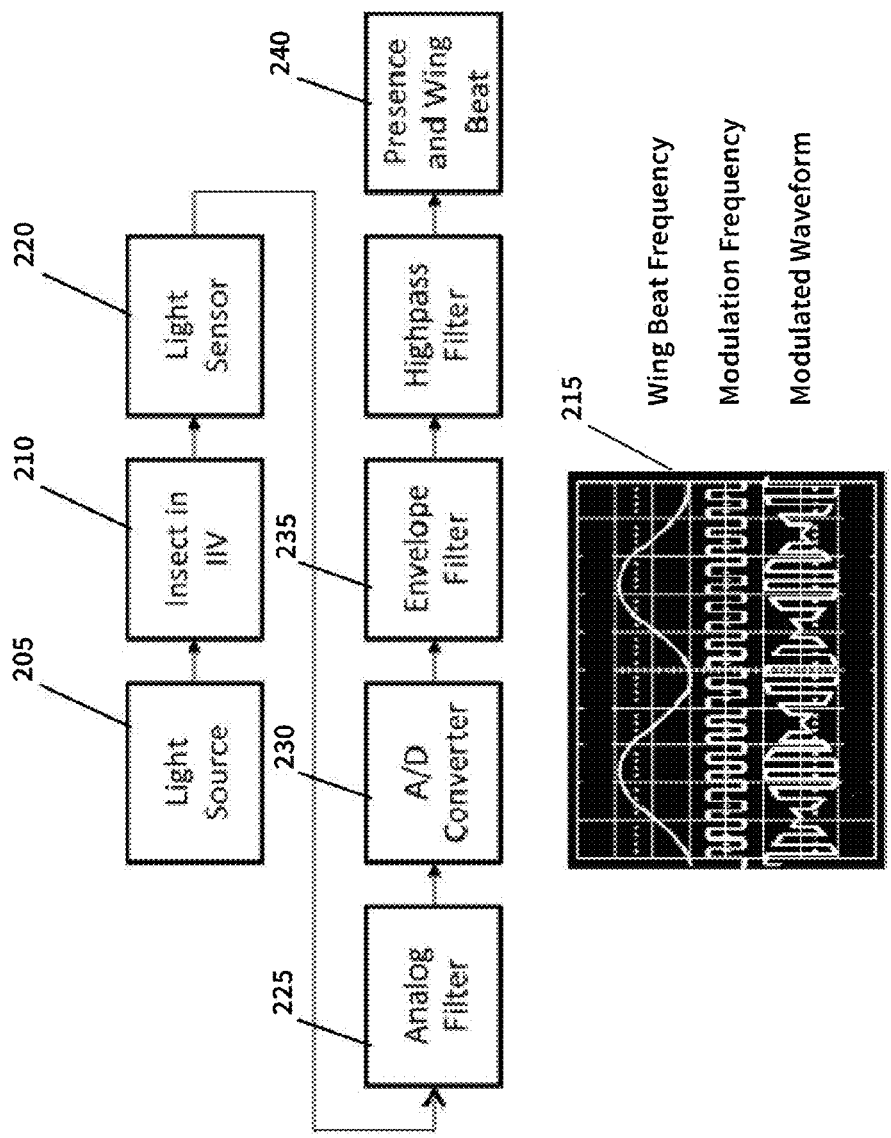
FIG. 2 is a schematic flow diagram of an example controller and object detection method for use in accordance with the present technology.

Referring now to FIG. 2, in one embodiment, a wing beat frequency is determined as follows. A light source is illuminated in step 205. Next, an insect enters the interaction volume in step 210. In some embodiments, light source intensity is modulated by the controller 104 (FIG. 1), with a carrier frequency higher than the wing beat frequency of the insect.

If an object insect is present, the carrier frequency is modulated by the wing beat frequency resulting in sensed light at the light sensor 110 having an intensity waveform as illustrated in graph 215.

An ambient light background may be also present but is not modulated. This waveform is detected by the light sensor 110 in step 220. The light is conditioned (a high-pass filter or a band-pass filter allowing only signal at the modulation frequency to pass) in step 225 using the analog filter and converted into digital form by an A/D converter of the multi-level type in step 230.

An envelope filter removes the carrier frequency from the modulated waveform in step 235. The wing beat frequency then appears on the output and is subjected to further signal processing to extract the insect present signal as well as a numerical value for the wing beat frequency in step 240.

Figure 3:
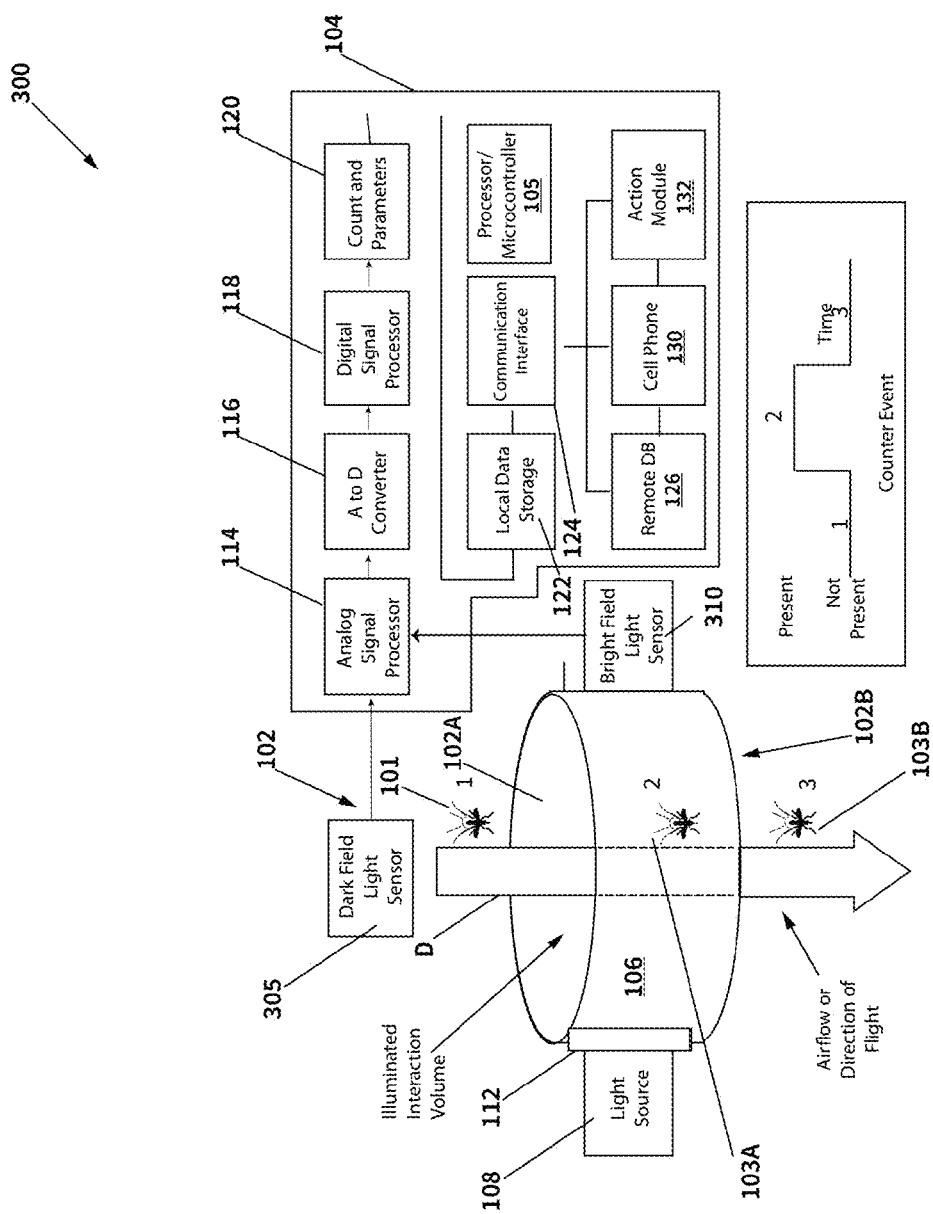
FIG. 3 is a schematic diagram of another example object detection system of the present technology.

FIG. 3 is another example object detection device 300 that is similar to the device 100 of FIG. 1 with the exception that the light sensor of the device 300 is divided between a dark field light sensor 305 and a bright field light sensor 310.

Figure 4:
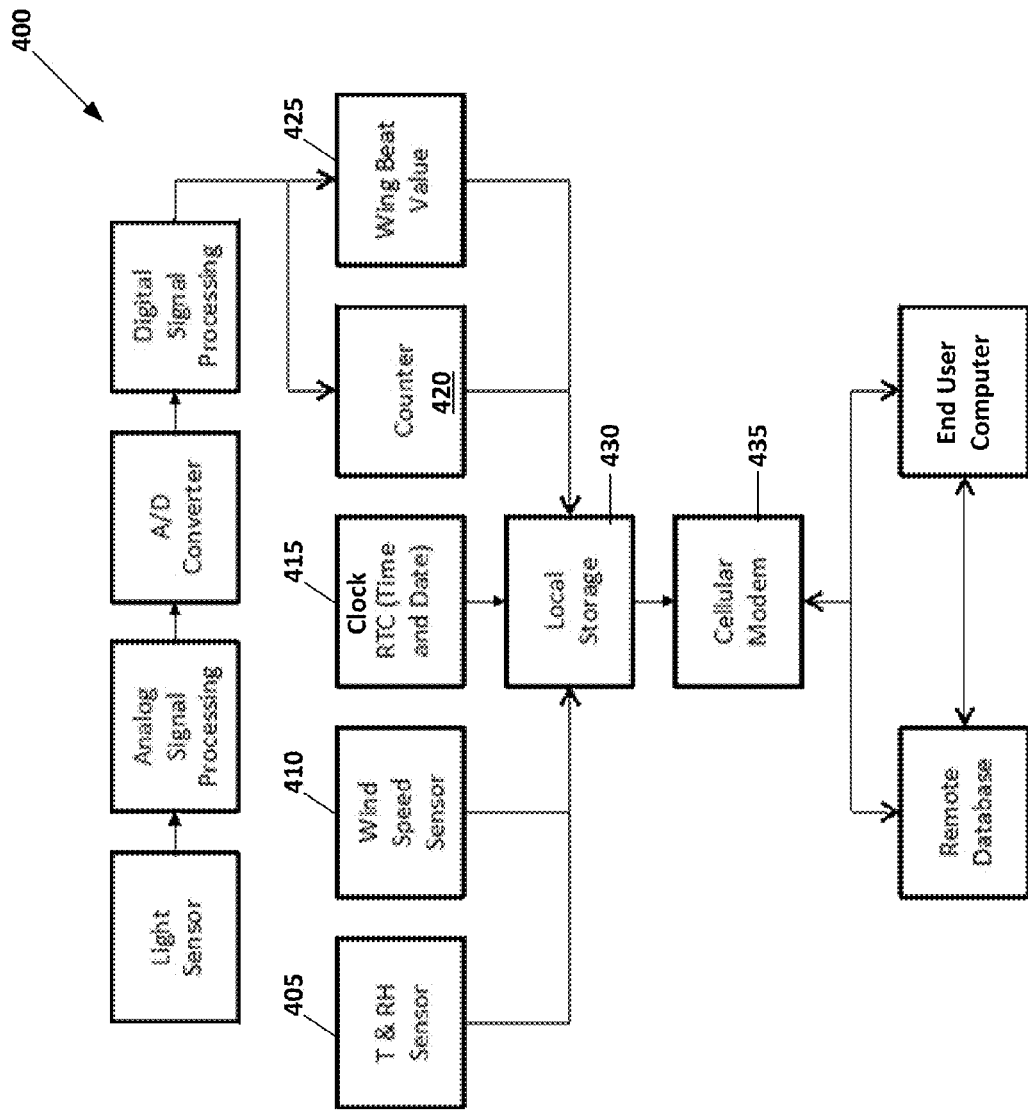
FIG. 4 is a schematic flow diagram of another example controller and object detection method for use in accordance with the present technology.

FIG. 4 illustrates signal and data flow in one embodiment of the present technology, using another example device 400. The device 400 of FIG. 4 is similar to the device 100 of FIG. 1 with the exception that several additional modules are present. In particular, the device 400 comprises temperature and relative humidity sensors 405, a wind speed sensor 410, and a clock 415 for time and date stamping data.

In one embodiment, the device 400 comprises at least one environmental sensor from the list comprising temperature and humidity, day light, rain fall amount, cloud cover, wind speed and wind direction —just to name a few.

To be sure, light intensity is measured and processed by the device 400 using any of the aforementioned processes. These signals are used by counter 420 and wing beat value 425 modules. Information from the temperature and relative humidity sensors 405, a wind speed sensor 410, counter module 420 and wing beat value module 425 is stored in local storage 430. Again, this information can also be transmitted using the communication module, such as a cellular modem 435 (or other wired or wireless communications module), providing data to a remote database or end user computer such as a cell phone, Smartphone, laptop, PC, server, or other computing device.

Figure 5:
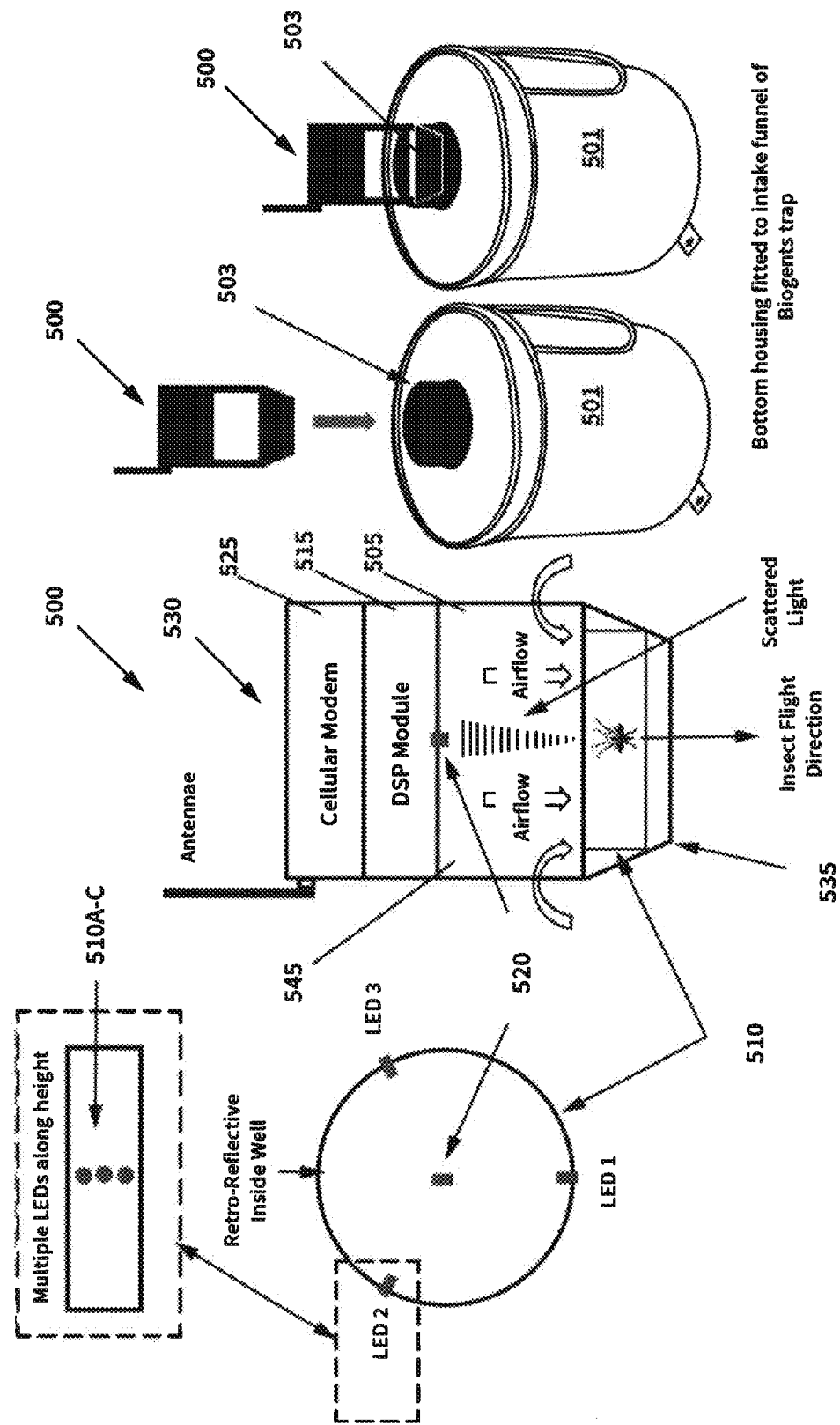
FIG. 5 is a schematic diagram of another example object detection system of the present technology.

Referring now to FIG. 5, another example device 500 is illustrated. An interaction volume 505 is a plastic cylinder of a diameter of about 11+/−2.5 cm and a height of about 2.5 cm which is easily fitted to existing insect trap 501 such as the mosquito traps type Sentinel™ or Mosquitaire™, manufactured by Biogents™, Regensburg, Germany. The device employs a fan to generate airflow to draw insects into a catch container or net inside. The device 500 also comprises a 12V power supply to which the device 500 is connected and draws its power.

A light source 510 comprises infrared LEDs at a peak emission wavelength of about 940 nm (NTE3027 or similar) mounted to the interaction volume 505 at three locations (Location 1, 2 and 3) about 120 degrees apart, facing inward. Each location such as Location 2, comprises three LEDs 510A-C, along a height. In some embodiments, each LED emits a cone of light with a half-power angle of about 45 degrees. The cones partially overlap and the entire interaction volume 505 is flooded with LED light. The LEDs are modulated at a frequency of about 10 kHz, i.e. about ten times a typical mosquito wing beat frequency using a DSP (digital signal processing) module 515. The DSP module 515 comprises a microcontroller.

The inside of the interaction volume 505 comprises a retro-reflective surface reflecting the radiation emitted by each LED rearwardly to increase the light intensity inside the interaction volume 505. In one embodiment, retro-reflective tape is applied to the inside of the interaction volume 505.

A light sensor 520 comprises a phototransistor (type NTE3033 or similar) and is mounted to the bottom of the DSP module 515, in the center of the interaction volume 505 and facing downwardly. The light sensor 520 has a nominal collection angle of about 65 degrees. In order to obtain a full cross-sectional view of the illuminated interaction volume, the light sensor 520 is mounted approximately 11 cm above the top of the interaction volume 505.

This embodiment utilizes a dark field method for detecting light. For example, if an insect is present, it reflects or scatters light towards the light sensor 520.

A cellular modem module 525 is provided in the device 500 and is combined with the microcontroller, both being packaged in a waterproof upper housing 530 that is appropriate for an outdoor environment. The microcontroller also provides local storage for insect count and other parameters, as well as a USB connection for communication with a PC or handheld device, and a removable flash card for extended local storage.

The interaction volume 505 and light source 510 are mounted inside a bottom housing 535 that is fitted to an intake funnel 503 of a trap 501. The upper housing is attached about 11+/−5 cm above the bottom housing using three posts. This construction allows the airflow generated by a fan inside the trap to flow into the interaction volume 505 unimpeded.

A space 545 between the bottom housing and the upper housing is selectively adjustable to optimize sensitivity.

Figure 6:
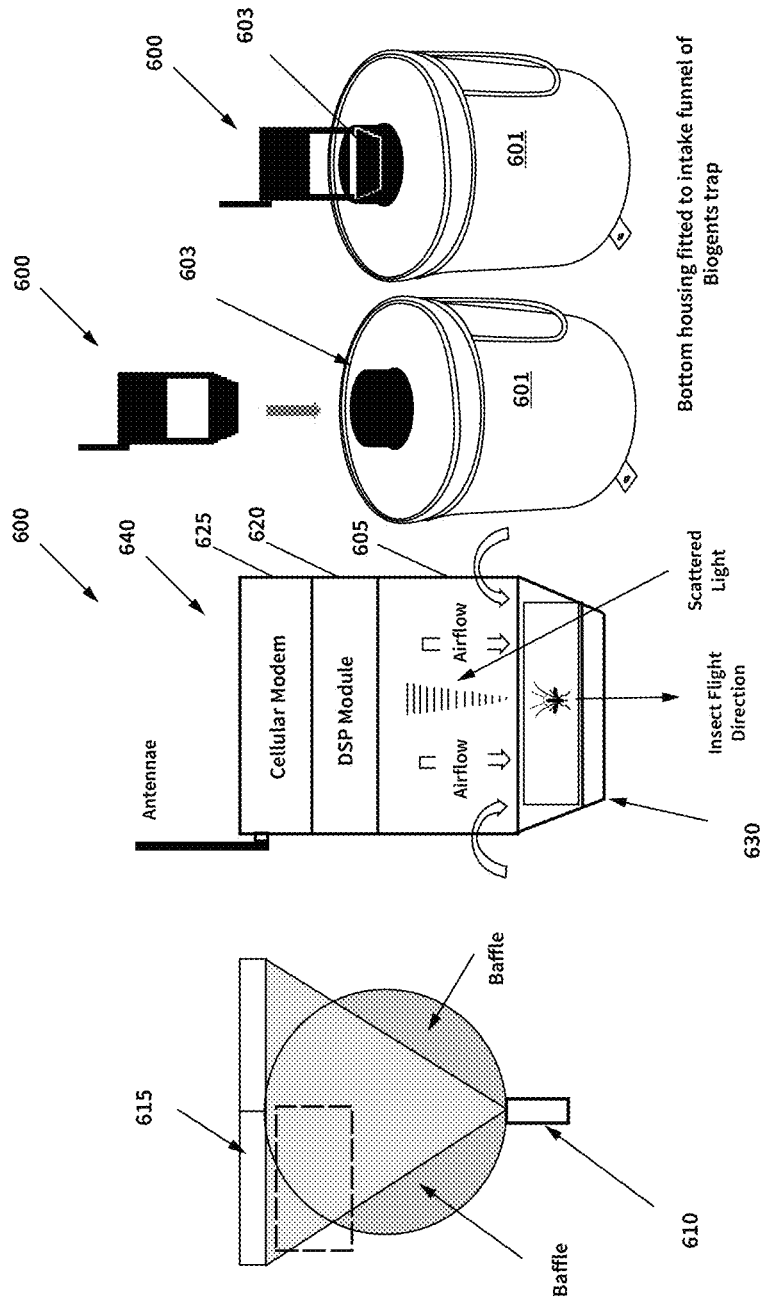
FIG. 6 is a schematic diagram of yet another example object detection system of the present technology.

Referring now to FIG. 6, another example device 600 is illustrated. The device 600 comprises an interaction volume 605 (shown in top view on the left), which comprises a plastic cylinder of a diameter of about 11+/−2.5 cm and a height of about 2.5 cm. This device is easily fitted to an existing insect trap 601 such as the mosquito traps type Sentinel™ or Mosquitaire™, manufactured by Biogents™, Regensburg, Germany. The device 600 uses a fan to generate airflow to draw insects into a catch container or net inside. They also comprise a 12V power supply to which a device 600 according to the present invention is connected and draws its power.

A light source 610, such as a line laser with a wavelength of 650 nm and a power of 5 mW is provided in the device 600. The light detector 615 is a solar panel of the type, such as an IXYS SLMD121H09L (nine light-sensitive elements connected in series). In one embodiment, the device uses analog signal processing comprising an active Sallen-Key high-pass filter with a cut-off of 23 Hz to filter out the constant background from the light source 610 and the ambient environment, as well as amplification of light intensity signals.

A DSP module 620 comprises a microcontroller, and a cellular modem module 625 comprises a cellular modem in communication with the microcontroller, both packaged in a waterproof upper housing appropriate for an outdoor environment. The microcontroller also provides local storage for insect count and other parameters, as well as a USB connection for communication with a PC or handheld device, and a removable flash card for extended local storage.

The interaction volume 605 and light source 610 are mounted inside a bottom housing 630 that is fitted to an intake funnel 603 of a trap 601. An upper housing 640 is attached about 11+/−5 cm above the bottom housing 630 using three posts. This construction allows the airflow generated by the fan inside the trap to flow into the illuminated interaction volume unimpeded. As with the device 500 of FIG. 5, a space between the bottom housing and the upper housing is adjustable to optimize sensitivity.

Figure 7:
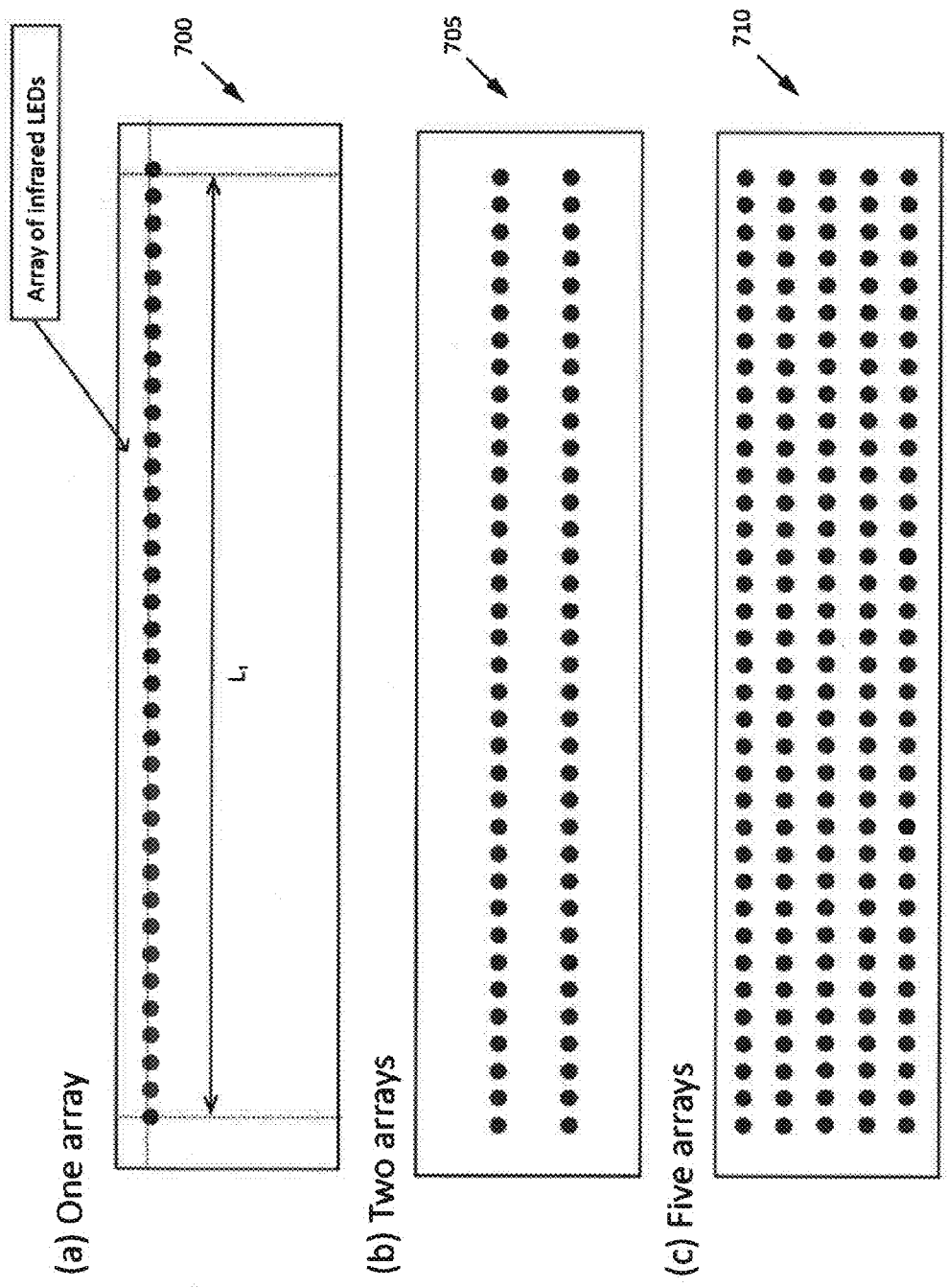
FIG. 7 illustrates a plurality of example light sources.

FIG. 7 illustrates various arrays used in light sources. Light source 700 includes a linear array of LEDs. Light source 705 comprises two linear arrays of LEDs. Linear array 710 comprises five linear arrays of LEDs.

Figure 8:
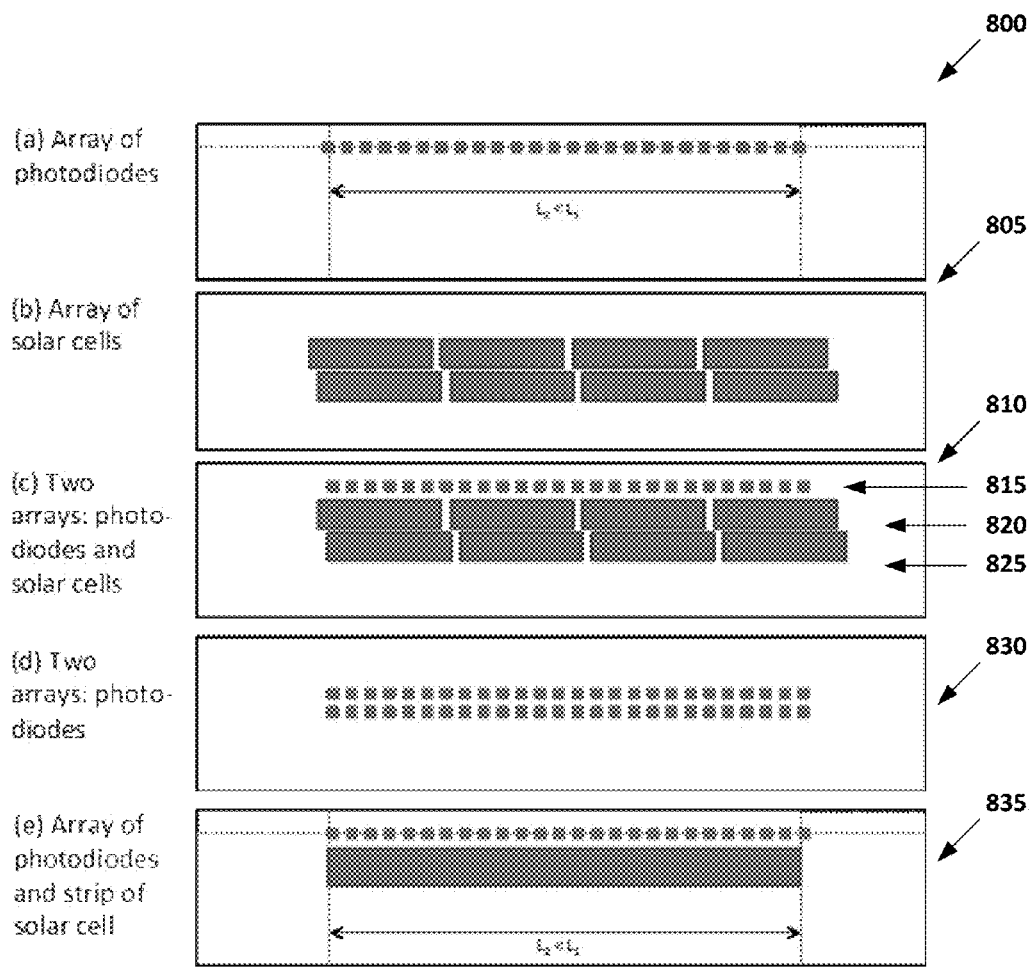
FIG. 8 illustrates a plurality of example light detectors.

FIG. 8 illustrates various arrays used in light sensors. Light sensor 800 comprises a linear array of photodiodes. Light sensor 805 comprises two linear arrays of solar cells. Light sensor 810 comprises a linear array of photodiodes 815 and two linear arrays of solar cells 820 and 825.

Light sensor 830 comprises two linear arrays of photodiodes. Light sensor 835 comprises a linear array of photodiodes and a single solar cell that extends the length of the light sensor 835.

Figure 9:
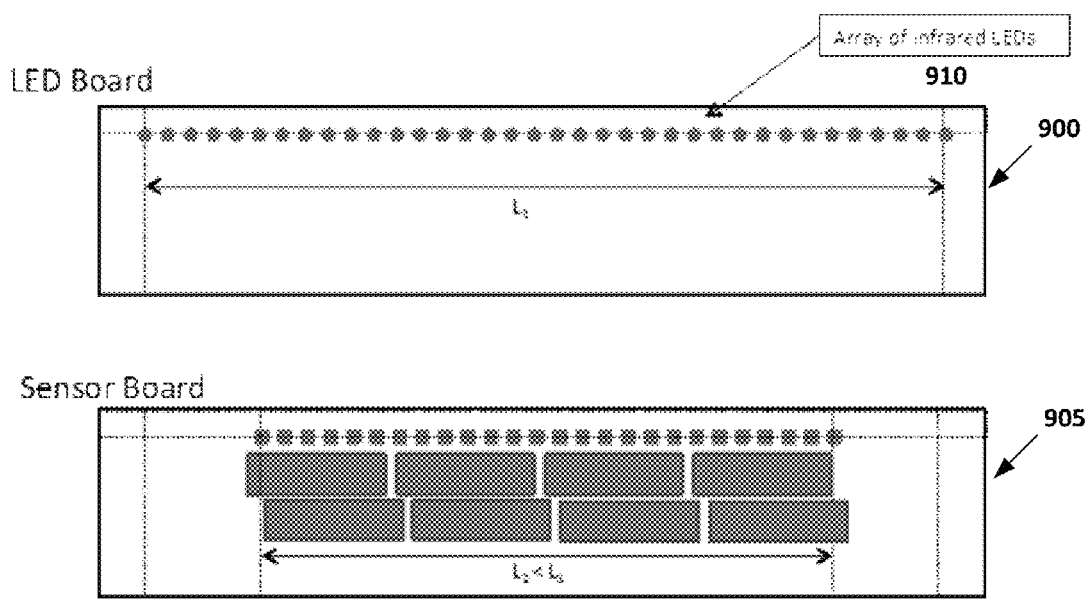
FIG. 9 illustrates a selection of an example light source and an example light detector for use in an object detection system.
Figure 10:
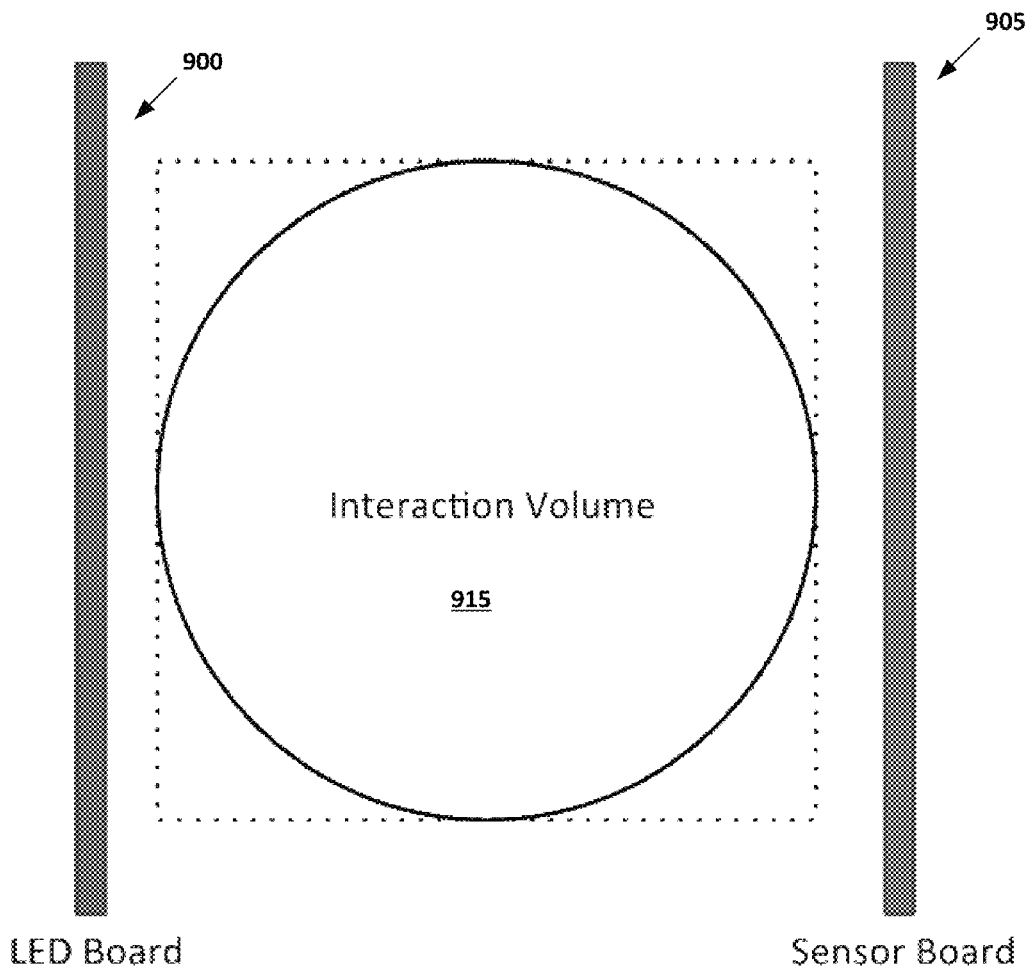
FIG. 10 is a top down view of an object detection system using the example light source and example light detector of FIG. 9.
Figure 11:
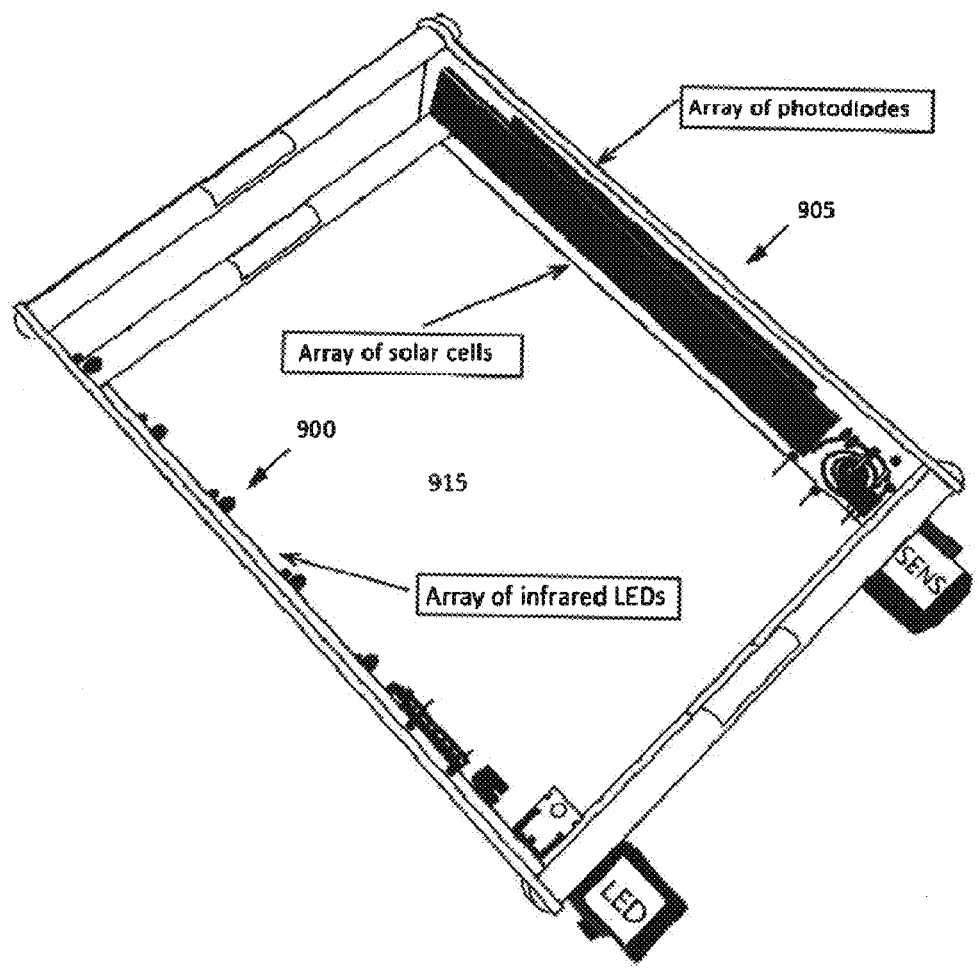
FIG. 11 is a perspective view of the object detection system of FIG. 10.

FIG. 9 illustrates an example selection of a matched light source 900 and light sensor 905. The light source 900 comprises a linear array of LEDs 910. The light sensor 905 comprises two linear arrays of solar cells and a linear array of photodiodes. In order to achieve uniform sensitivity, the length $L_1$ of the LED array exceeds the length $L_2$ of the detector arrays. The light source 900 and light sensor 905 are configured for use in an interaction volume 915, as illustrated in FIG. 10 and FIG. 11.

As an example, in order to obtain an interaction volume 915 with uniform sensitivity, the following design can be employed. The light source is a strip of infrared LEDs emitting at 875 nm mounted to a printed circuit board (PCB) of dimensions 164×35 mm (LED width: 2.34 mm (max); LED height: 2.16 mm (max); Pitch: 5.0 mm; Total width: 147.34 mm [(30−1)×5+2.34]; Center line: 5 mm from top edge; Middle at 82 mm from left/right edge).

Six strings of five LEDs in series are connected to a current controller. The light sensor 905 comprises two channels. A first channel comprises a strip of infrared photodiodes and a second channel comprises two rows of solar cells. These channels are mounted to a printed circuit board (PCB) of dimensions 164×35 mm.

With respect to channel one: photodiode width: 2.34 mm (max); photodiode height: 2.16 mm (max); Pitch: 2.5 mm; Total width: 102.34 mm [(41−1)×2.5+2.34]; Center line: 5 mm from top edge; Middle at 82 mm from left/right edge. With respect to channel two: 10× Si Solar Cell; Width: 22 mm; Height: 7.5 mm; Pitch: 23 mm; Offset top to bottom row: 5 mm; White stripe is cathode (−); Total width: 117 mm; Top: 10 mm from PCB top edge; Middle at 82 mm from left/right edge.

In some embodiments, the LED array is longer than the sensor array by about 50%, which results in uniform illumination of the interaction volume and the sensor array, resulting in uniform intensity.

Figure 12:
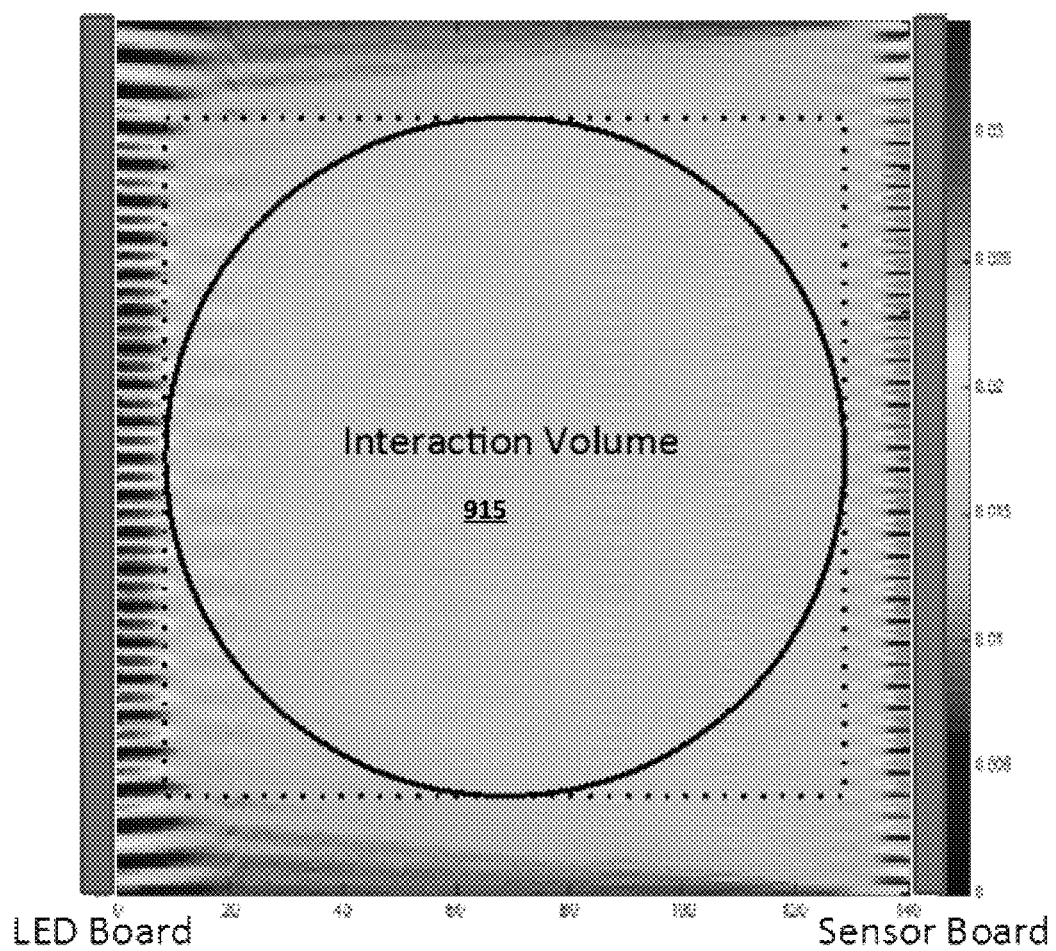
FIG. 12 is a light intensity model of the object detection system of FIGS. 10-11.

The photodiode array and the solar cell array are each wired in parallel, which results in uniform, smooth sensitivity, as evidenced in a model of FIG. 12, even with gaps between individual LEDs and sensor elements (or "pixels"). These particular configurations provide unexpected results in their remarkable uniformity with respect to light intensity.

FIG. 12 illustrates a graphical model of the device of FIGS. 9-11. The model illustrates that even with the discrete nature and small area of the LEDs and photodiodes, smooth and uniform sensitivity is obtained for objects passing through the interaction volume. As an object travels through the interaction volume perpendicular to the plane defined by the light sources and detectors, part of the light from the illumination is obscured, resulting in a change of light hitting the detector. This light change is detected and processed using any of the methods described above. The aspect of uniform sensitivity allows object size classification by light intensity changes.

Figure 13:
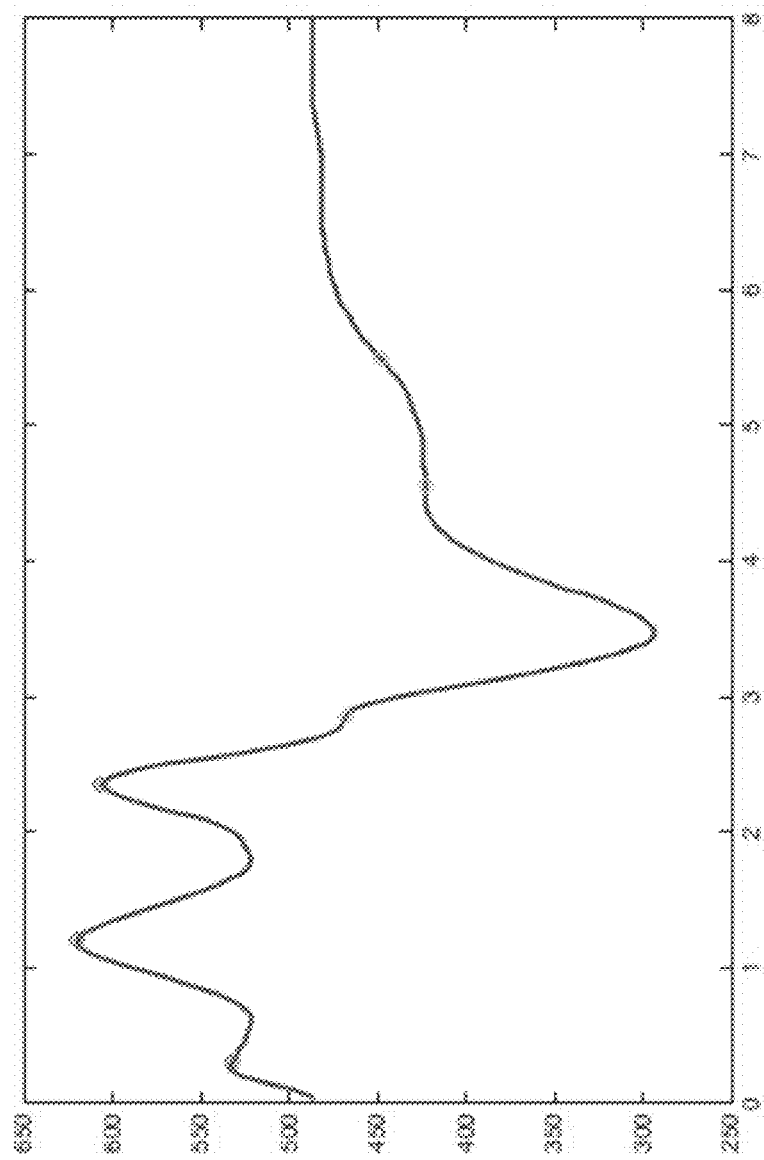
FIGS. 13 and 14 are graphs illustrating the detection of insects (e.g., objects within the object detection system of FIGS. 10-11.

FIG. 13 is a graph obtained using the device of FIGS. 9-11. The graph illustrates a signal that was obtained from the photodiode array with a mosquito passing through the interaction volume. The size of its shadow changes as it beats its wings. This wingbeat modulation is clearly visible. Also, the amplitude of the signal depends on the size of the object. Both signal amplitude and modulations are used to distinguish different type of insects, and to distinguish living objects (e.g. insects) from inanimate objects (e.g. raindrops).

Figure 14:
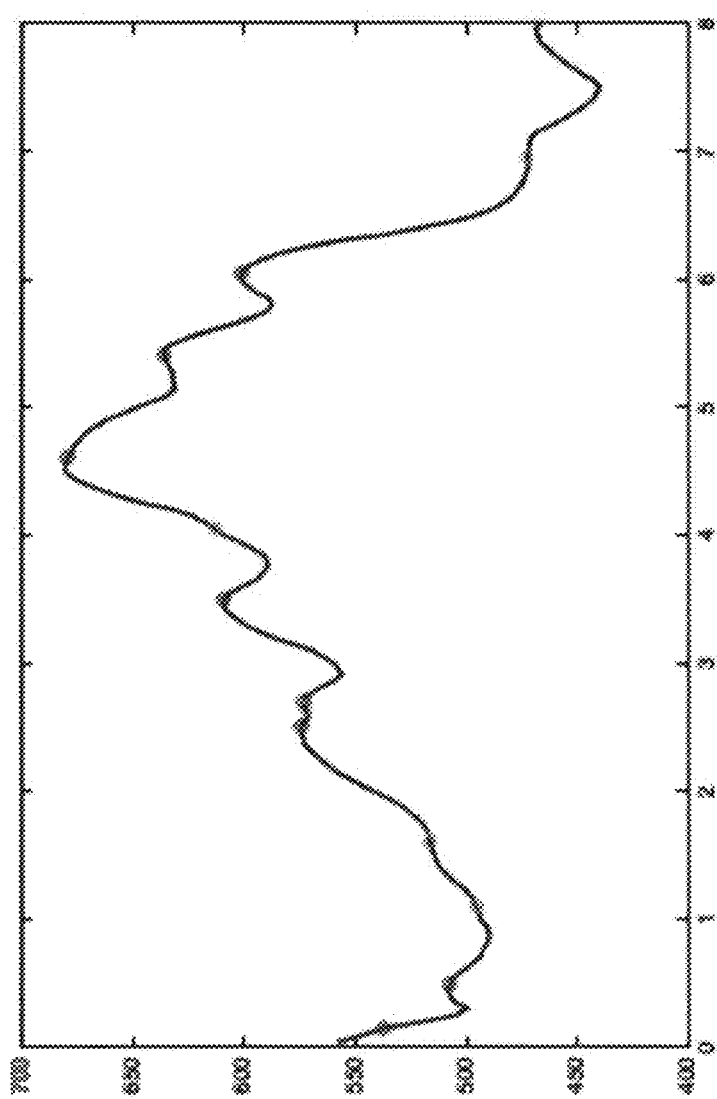

FIG. 14 is another graph obtained using the device of FIGS. 9-11. The graph illustrates a signal that was obtained from the solar cell array. Since the solar cells are larger, a signal is recorded for a longer time, so more cycles of the modulation due to wingbeat can be observed and be used for discrimination between different kinds of insects.

Figure 15:
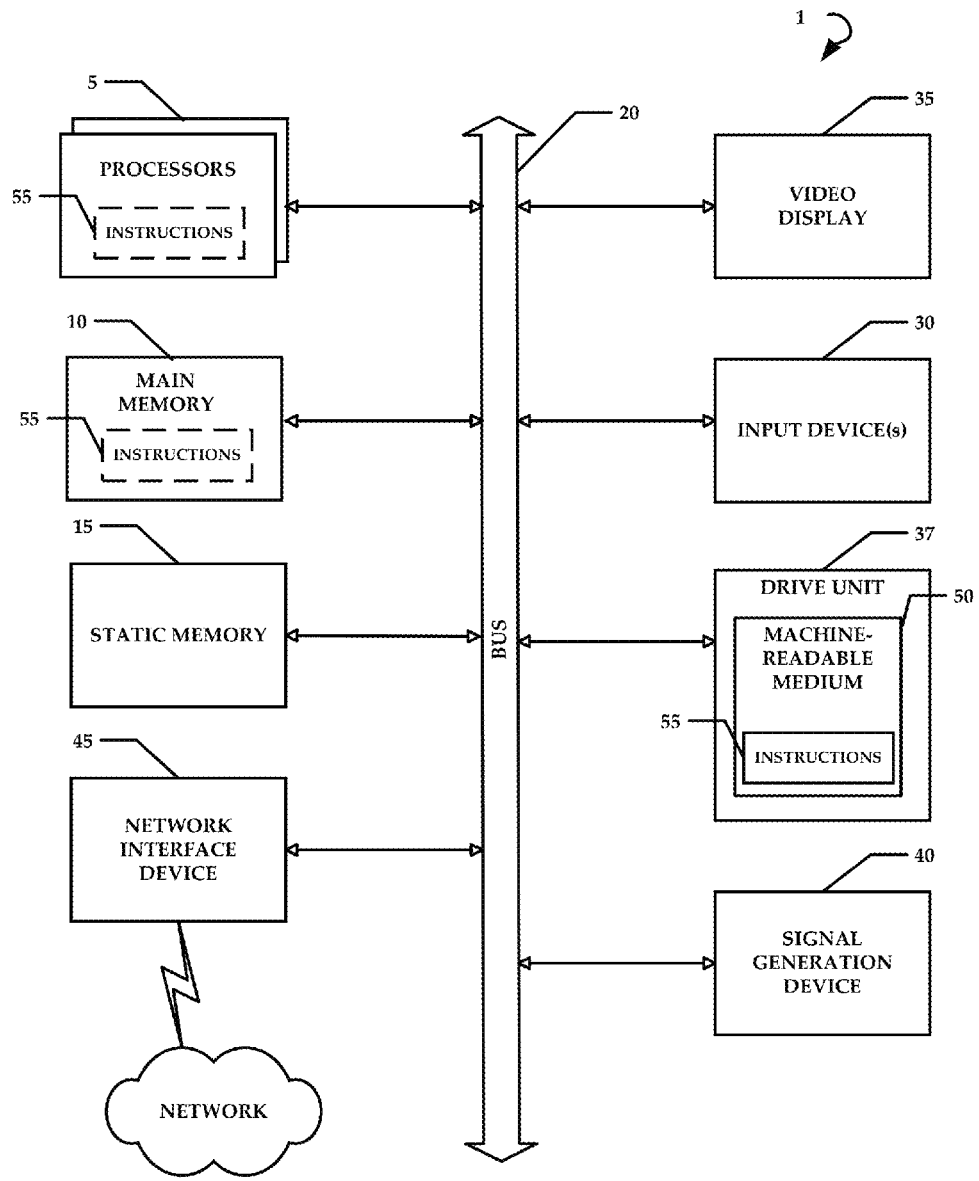
FIG. 15 is a diagrammatic representation of an example machine in the form of a computer system that can be used to implement aspects of the present technology.

FIG. 15 is a diagrammatic representation of an example machine in the form of a computer system 1, within which a set of instructions for causing the machine to perform any one or more of the methodologies discussed herein may be executed. In various example embodiments, the machine operates as a standalone device or may be connected (e.g., networked) to other machines. In a networked deployment, the machine may operate in the capacity of a server or a client machine in a server-client network environment, or as a peer machine in a peer-to-peer (or distributed) network environment. The machine may be a robotic construction marking device, a base station, a personal computer (PC), a tablet PC, a set-top box (STB), a personal digital assistant (PDA), a cellular telephone, a portable music player (e.g., a portable hard drive audio device such as an Moving Picture Experts Group Audio Layer 3 (MP3) player), a web appliance, a network router, switch or bridge, or any machine capable of executing a set of instructions (sequential or otherwise) that specify actions to be taken by that machine. Further, while only a single machine is illustrated, the term "machine" shall also be taken to include any collection of machines that individually or jointly execute a set (or multiple sets) of instructions to perform any one or more of the methodologies discussed herein.

The example computer system 1 includes a processor or multiple processors 5 (e.g., a central processing unit (CPU), a graphics processing unit (GPU), or both), and a main memory 10 and static memory 15, which communicate with each other via a bus 20. The computer system 1 may further include a video display 35 (e.g., a liquid crystal display (LCD)). The computer system 1 may also include an alpha-numeric input device(s) 30 (e.g., a keyboard), a cursor control device (e.g., a mouse), a voice recognition or biometric verification unit (not shown), a drive unit 37 (also referred to as disk drive unit), a signal generation device 40 (e.g., a speaker), and a network interface device 45. The computer system 1 may further include a data encryption module (not shown) to encrypt data.

The disk drive unit 37 includes a computer or machine-readable medium 50 on which is stored one or more sets of instructions and data structures (e.g., instructions 55) embodying or utilizing any one or more of the methodologies or functions described herein. The instructions 55 may also reside, completely or at least partially, within the main memory 10 and/or within the processors 5 during execution thereof by the computer system 1. The main memory 10 and the processors 5 may also constitute machine-readable media.

The instructions 55 may further be transmitted or received over a network via the network interface device 45 utilizing any one of a number of well-known transfer protocols (e.g., Hyper Text Transfer Protocol (HTTP)). While the machine-readable medium 50 is shown in an example embodiment to be a single medium, the term "computer-readable medium" should be taken to include a single medium or multiple media (e.g., a centralized or distributed database and/or associated caches and servers) that store the one or more sets of instructions. The term "computer-readable medium" shall also be taken to include any medium that is capable of storing, encoding, or carrying a set of instructions for execution by the machine and that causes the machine to perform any one or more of the methodologies of the present application, or that is capable of storing, encoding, or carrying data structures utilized by or associated with such a set of instructions. The term "computer-readable medium" shall accordingly be taken to include, but not be limited to, solid-state memories, optical and magnetic media, and carrier wave signals. Such media may also include, without limitation, hard disks, floppy disks, flash memory cards, digital video disks, random access memory (RAM), read only memory (ROM), and the like. The example embodiments described herein may be implemented in an operating environment comprising software installed on a computer, in hardware, or in a combination of software and hardware.

Not all components of the computer system 1 are required and thus portions of the computer system 1 can be removed if not needed, such as I/O devices.

The corresponding structures, materials, acts, and equivalents of all means or step plus function elements in the claims below are intended to include any structure, material, or act for performing the function in combination with other claimed elements as specifically claimed. The description of the present technology has been presented for purposes of illustration and description, but is not intended to be exhaustive or limited to the present technology in the form disclosed. Many modifications and variations will be apparent to those of ordinary skill in the art without departing from the scope and spirit of the present technology. Exemplary embodiments were chosen and described in order to best explain the principles of the present technology and its practical application, and to enable others of ordinary skill in the art to understand the present technology for various embodiments with various modifications as are suited to the particular use contemplated.

Aspects of the present technology are described above with reference to flowchart illustrations and/or block diagrams of methods, apparatus (systems) and computer program products according to embodiments of the present technology. It will be understood that each block of the flowchart illustrations and/or block diagrams, and combinations of blocks in the flowchart illustrations and/or block diagrams, can be implemented by computer program instructions. These computer program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks.

These computer program instructions may also be stored in a computer readable medium that can direct a computer, other programmable data processing apparatus, or other devices to function in a particular manner, such that the instructions stored in the computer readable medium produce an article of manufacture including instructions which implement the function/act specified in the flowchart and/or block diagram block or blocks.

The computer program instructions may also be loaded onto a computer, other programmable data processing apparatus, or other devices to cause a series of operational steps to be performed on the computer, other programmable apparatus or other devices to produce a computer implemented process such that the instructions which execute on the computer or other programmable apparatus provide processes for implementing the functions/acts specified in the flowchart and/or block diagram block or blocks.

The flowchart and block diagrams in the Figures illustrate the architecture, functionality, and operation of possible implementations of systems, methods and computer program products according to various embodiments of the present technology. In this regard, each block in the flowchart or block diagrams may represent a module, segment, or portion of code, which comprises one or more executable instructions for implementing the specified logical function(s). It should also be noted that, in some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts, or combinations of special purpose hardware and computer instructions.

In the following description, for purposes of explanation and not limitation, specific details are set forth, such as particular embodiments, procedures, techniques, etc. in order to provide a thorough understanding of the present invention. However, it will be apparent to one skilled in the art that the present invention may be practiced in other embodiments that depart from these specific details.

Reference throughout this specification to "one embodiment" or "an embodiment" means that a particular feature, structure, or characteristic described in connection with the embodiment is included in at least one embodiment of the present invention. Thus, the appearances of the phrases "in one embodiment" or "in an embodiment" or "according to one embodiment" (or other phrases having similar import) at various places throughout this specification are not necessarily all referring to the same embodiment. Furthermore, the particular features, structures, or characteristics may be combined in any suitable manner in one or more embodiments. Furthermore, depending on the context of discussion herein, a singular term may include its plural forms and a plural term may include its singular form. Similarly, a hyphenated term (e.g., "on-demand") may be occasionally interchangeably used with its non-hyphenated version (e.g., "on demand"), a capitalized entry (e.g., "Software") may be interchangeably used with its non-capitalized version (e.g., "software"), a plural term may be indicated with or without an apostrophe (e.g., PE's or PEs), and an italicized term (e.g., "N+1") may be interchangeably used with its non-italicized version (e.g., "N+1"). Such occasional interchangeable uses shall not be considered inconsistent with each other.

Also, some embodiments may be described in terms of "means for" performing a task or set of tasks. It will be understood that a "means for" may be expressed herein in terms of a structure, such as a processor, a memory, an I/O device such as a camera, or combinations thereof. Alternatively, the "means for" may include an algorithm that is descriptive of a function or method step, while in yet other embodiments the "means for" is expressed in terms of a mathematical formula, prose, or as a flow chart or signal diagram.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

It is noted at the outset that the terms "coupled," "connected", "connecting," "electrically connected," etc., are used interchangeably herein to generally refer to the condition of being electrically/electronically connected. Similarly, a first entity is considered to be in "communication" with a second entity (or entities) when the first entity electrically sends and/or receives (whether through wireline or wireless means) information signals (whether containing data information or non-data/control information) to the second entity regardless of the type (analog or digital) of those signals. It is further noted that various figures (including component diagrams) shown and discussed herein are for illustrative purpose only, and are not drawn to scale.

If any disclosures are incorporated herein by reference and such incorporated disclosures conflict in part and/or in whole with the present disclosure, then to the extent of conflict, and/or broader disclosure, and/or broader definition of terms, the present disclosure controls. If such incorporated disclosures conflict in part and/or in whole with one another, then to the extent of conflict, the later-dated disclosure controls.

The terminology used herein can imply direct or indirect, full or partial, temporary or permanent, immediate or delayed, synchronous or asynchronous, action or inaction. For example, when an element is referred to as being "on," "connected" or "coupled" to another element, then the element can be directly on, connected or coupled to the other element and/or intervening elements may be present, including indirect and/or direct variants. In contrast, when an element is referred to as being "directly connected" or "directly coupled" to another element, there are no intervening elements present.

Although the terms first, second, etc. may be used herein to describe various elements, components, regions, layers and/or sections, these elements, components, regions, layers and/or sections should not necessarily be limited by such terms. These terms are only used to distinguish one element, component, region, layer or section from another element, component, region, layer or section. Thus, a first element, component, region, layer or section discussed below could be termed a second element, component, region, layer or section without departing from the teachings of the present disclosure.

The terminology used herein is for the purpose of describing particular embodiments only and is not intended to be necessarily limiting of the disclosure. As used herein, the singular forms "a," "an" and "the" are intended to include the plural forms as well, unless the context clearly indicates otherwise. The terms "comprises," "includes" and/or "comprising," "including" when used in this specification, specify the presence of stated features, integers, steps, operations, elements, and/or components, but do not preclude the presence or addition of one or more other features, integers, steps, operations, elements, components, and/or groups thereof.

Example embodiments of the present disclosure are described herein with reference to illustrations of idealized embodiments (and intermediate structures) of the present disclosure. As such, variations from the shapes of the illustrations as a result, for example, of manufacturing techniques and/or tolerances, are to be expected. Thus, the example embodiments of the present disclosure should not be construed as necessarily limited to the particular shapes of regions illustrated herein, but are to include deviations in shapes that result, for example, from manufacturing.

Any and/or all elements, as disclosed herein, can be formed from a same, structurally continuous piece, such as being unitary, and/or be separately manufactured and/or connected, such as being an assembly and/or modules. Any and/or all elements, as disclosed herein, can be manufactured via any manufacturing processes, whether additive manufacturing, subtractive manufacturing and/or other any other types of manufacturing. For example, some manufacturing processes include three dimensional (3D) printing, laser cutting, computer numerical control (CNC) routing, milling, pressing, stamping, vacuum forming, hydroforming, injection molding, lithography and/or others.

Any and/or all elements, as disclosed herein, can include, whether partially and/or fully, a solid, including a metal, a mineral, a ceramic, an amorphous solid, such as glass, a glass ceramic, an organic solid, such as wood and/or a polymer, such as rubber, a composite material, a semiconductor, a nano-material, a biomaterial and/or any combinations thereof. Any and/or all elements, as disclosed herein, can include, whether partially and/or fully, a coating, including an informational coating, such as ink, an adhesive coating, a melt-adhesive coating, such as vacuum seal and/or heat seal, a release coating, such as tape liner, a low surface energy coating, an optical coating, such as for tint, color, hue, saturation, tone, shade, transparency, translucency, non-transparency, luminescence, anti-reflection and/or holographic, a photo-sensitive coating, an electronic and/or thermal property coating, such as for passivity, insulation, resistance or conduction, a magnetic coating, a water-resistant and/or waterproof coating, a scent coating and/or any combinations thereof.

Unless otherwise defined, all terms (including technical and scientific terms) used herein have the same meaning as commonly understood by one of ordinary skill in the art to which this disclosure belongs. The terms, such as those defined in commonly used dictionaries, should be interpreted as having a meaning that is consistent with their meaning in the context of the relevant art and should not be interpreted in an idealized and/or overly formal sense unless expressly so defined herein.

Furthermore, relative terms such as "below," "lower," "above," and "upper" may be used herein to describe one element's relationship to another element as illustrated in the accompanying drawings. Such relative terms are intended to encompass different orientations of illustrated technologies in addition to the orientation depicted in the accompanying drawings. For example, if a device in the accompanying drawings is turned over, then the elements described as being on the "lower" side of other elements would then be oriented on "upper" sides of the other elements. Similarly, if the device in one of the figures is turned over, elements described as "below" or "beneath" other elements would then be oriented "above" the other elements. Therefore, the example terms "below" and "lower" can, therefore, encompass both an orientation of above and below.

While various embodiments have been described above, it should be understood that they have been presented by way of example only, and not limitation. The descriptions are not intended to limit the scope of the invention to the particular forms set forth herein. To the contrary, the present descriptions are intended to cover such alternatives, modifications, and equivalents as may be included within the spirit and scope of the invention as defined by the appended claims and otherwise appreciated by one of ordinary skill in the art. Thus, the breadth and scope of a preferred embodiment should not be limited by any of the above-described exemplary embodiments.

What is claimed is:

1. An object detection system, comprising:
    an enclosure formed by a sidewall to define an interaction volume;
    at least one light source for illuminating the interaction volume with a light;
    at least one light sensor that senses disturbances in light intensity due to scattering, reflection, or absorption of the light by objects within the interaction volume; and
    a controller that is configured to detect an object or object behavior within the interaction volume based on the disturbances in the light intensity, wherein the controller is further configured to time stamp signals received from the at least one light sensor and wherein the objects are insects, further wherein the controller is further configured to detect and record a sequence, the sequence comprising a first time at which an insect is not present in the interaction volume, a second time at which an insect is present in the interaction volume, and a third time at which the insect is not present in the interaction volume, wherein detecting the sequence indicates a count of an insect in the interaction volume.

2. The system according to claim 1, wherein the controller is further configured to:
    modulate a frequency of the at least one light source to account for ambient light in the interaction volume; and
    detect interactions by the insect within the interaction volume by:
        detecting modifications of the modulated light by the objects; and
        differentiating the ambient light from the modulated light through signal processing.

3. The system according to claim 2, wherein a modulation frequency is chosen to be above a frequency of fluctuations or oscillations of the ambient light.

4. The system according to claim 3, wherein differentiating the ambient light from the modulated light through signal processing comprises suppressing a constant or variable background signal caused by an ambient light source, wherein the background signal comprises frequencies in a range of approximately 0 Hz to approximately 120 Hz, inclusive.

5. The system according to claim 1, wherein the at least one light sensor comprises at least one of:
    a bright field sensor disposed in a location inside or near the sidewall of the interaction volume so as to allow the light to contact the bright field sensor, the bright field sensor indicating a reduction in the light intensity of the light; and
    a dark field sensor disposed in a location inside or near the sidewall of the interaction volume so as to prevent the light from contacting the dark field sensor, the dark field sensor indicating an increase in the light intensity of the light.

6. The system according to claim 1, wherein the controller is further configured to detect a size of the objects.

7. The system according to claim 1, wherein the at least one light source comprises a plurality of light sources, the controller is further configured to modulate a frequency of light emitted by each of the plurality of light sources such that the frequency of each of the plurality of light sources is different from one another.

8. The system according to claim 7, wherein the at least one light sensor comprises a plurality of light sensors, wherein each of the plurality of light sensors has a maximum sensitivity near a peak emission of at least one of the plurality of light sources.

9. The system according to claim 1, further comprising an attracting light source.

10. The system according to claim 1, wherein the at least one light sensor is positioned in a location comprising any of:
    a location suitable for sensing light that passes through and exits the interaction volume;
    a location suitable for sensing light scattered or reflected but not light passing through and exiting the interaction volume; and
    a location for sensing the light intensity present in the interaction volume.

11. The system according to claim 1, wherein the at least one light sensor has a spectral sensitivity response with a maximum near a peak emission of a light source.

12. The system according to claim 1, wherein the objects are insects, further wherein the controller is further configured to calculate a wing beat frequency of an insect by:
    modulating the light intensity of the at least one light source with a carrier frequency that is higher than the wing beat frequency of the insect to create a modulated waveform; and
    detecting a waveform of light that is resultant from a modulation of the carrier frequency by the wing beat frequency.

13. The system according to claim 12, wherein the controller comprises an envelope filter that removes the carrier frequency from the modulated waveform.

14. The system according to claim 1, wherein an inner surface of the enclosure is a retro-reflective surface reflecting the light emitted by the at least one light source.

15. The system according to claim 1, wherein the interaction volume comprises a funnel and a trap disposed on opposing ends of the interaction volume.

16. The system according to claim 1, wherein the at least one light source comprises any of a light emitting diode, a line laser, or combinations thereof.

17. The system according to claim 1, wherein the at least one light sensor comprises any of a photodiode, a phototransistor, a charge coupled device, a position-sensitive detector, a solar cell, a photovoltaic cell, an antenna, a thermopile, or any combinations thereof.

18. The system according to claim 1, wherein the at least one light sensor comprises an array comprising a plurality of individual photodiodes, the plurality of individual photodiodes being electrically coupled in series, at least one of the plurality of individual photodiodes is masked so as to receive less light than non-masked ones of the plurality of individual photodiodes in order to reduce a current through the array, which results in an increase in a sensitivity of the non-masked ones of the plurality of individual photodiodes.

19. An object detection system, comprising
a light source comprising a linear array of light emitting devices;
a light sensor comprising at least one linear array of light sensors, wherein at least one of the light sensors is masked so as to receive less light than non-masked ones of the light sensors in order to reduce a current through the array;
an interaction volume defined by a space between the light source and the at least one linear array of light sensors, wherein the space between the light source and the at least one linear array of light sensors allows for uniform light intensity throughout the interaction volume; and
wherein the at least one linear array of light sensors senses disturbances in the light intensity indicative of a presence of an object in the interaction volume.

20. The system according to claim 19, wherein the at least one linear array of light sensors comprises a row of photodiodes.

21. The system according to claim 19, wherein the at least one linear array of light sensors comprises two rows of solar cells, wherein the two rows of solar cells are offset from one another.

22. The system according to claim 19, further comprising a controller that is configured to:
modulate a frequency of the light source to account for ambient light in the interaction volume; and
detect interactions by the object within the interaction volume by:
detecting modifications of the modulated light by the object; and
differentiating the ambient light from the modulated light through signal processing.

23. The system according to claim 19, further comprising a temperature and relative humidity sensor.

24. The system according to claim 19, further comprising a wind speed sensor.

25. The system according to claim 22, wherein the controller uses a digital signal processor to:
modulate the light intensity of the light source with a carrier frequency that is higher than a wing beat frequency of an insect to create a modulated waveform, the object being the insect; and
detect a waveform of light that is resultant from a modulation of the carrier frequency by the wing beat frequency.

26. The system according to claim 19, further comprising a clock for time and date stamping signals output by the light sensor.

* * * * *